US012760372B2

(12) United States Patent
Di Fiore et al.

(10) Patent No.: US 12,760,372 B2
(45) Date of Patent: Oct. 13, 2026

(54) METHODS AND KITS FOR DETERMINING THE RISK OF BREAST CANCER RECURRENCE

(71) Applicants: Istituto Europeo di Oncologia S.r.l., Milan (IT); Universita degli Studi di Milano, Milan (IT)

(72) Inventors: Pier Paolo Di Fiore, Milan (IT); Salvatore Pece, Milan (IT)

(73) Assignee: Istituto Europeo di Oncologia S.r.l., Milan (IT)

( * ) Notice: Subject to any disclaimer, the term of this patent is extended or adjusted under 35 U.S.C. 154(b) by 761 days.

(21) Appl. No.: 17/907,601

(22) PCT Filed: May 7, 2021

(86) PCT No.: PCT/EP2021/062176
§ 371 (c)(1),
(2) Date: Sep. 28, 2022

(87) PCT Pub. No.: WO2021/224466
PCT Pub. Date: Nov. 11, 2021

(65) Prior Publication Data

US 2023/0143295 A1 May 11, 2023

(30) Foreign Application Priority Data

May 8, 2020 (EP) .................................... 20173612

(51) Int. Cl.
*C12Q 1/6886* (2018.01)
*G16H 50/30* (2018.01)

(52) U.S. Cl.
CPC ........... *C12Q 1/6886* (2013.01); *G16H 50/30* (2018.01); *C12Q 2600/118* (2013.01); *C12Q 2600/158* (2013.01)

(58) Field of Classification Search
CPC ...................................................... G16H 50/30
See application file for complete search history.

(56) References Cited

U.S. PATENT DOCUMENTS

| | | | |
|---|---|---|---|
| 5,188,934 | A | 2/1993 | Menchen et al. |
| 5,366,860 | A | 11/1994 | Bergot et al. |
| 5,411,876 | A | 5/1995 | Bloch et al. |
| 5,413,924 | A | 5/1995 | Kosak et al. |
| 5,432,272 | A | 7/1995 | Benner |
| 5,538,848 | A | 7/1996 | Livak et al. |
| 5,550,044 | A | 8/1996 | Kosak et al. |
| 5,800,996 | A | 9/1998 | Lee et al. |
| 5,847,162 | A | 12/1998 | Lee et al. |
| 5,863,727 | A | 1/1999 | Lee et al. |
| 5,925,517 | A | 7/1999 | Tyagi et al. |
| 5,936,087 | A | 8/1999 | Benson et al. |
| 5,945,526 | A | 8/1999 | Lee et al. |
| 5,965,364 | A | 10/1999 | Benner |
| 5,985,619 | A | 11/1999 | Sutherland et al. |
| 6,001,983 | A | 12/1999 | Benner |
| 6,008,379 | A | 12/1999 | Benson et al. |
| 6,020,481 | A | 2/2000 | Benson et al. |
| 6,051,719 | A | 4/2000 | Benson et al. |
| 6,103,476 | A | 8/2000 | Tyagi et al. |
| 6,140,054 | A | 10/2000 | Wittwer et al. |
| 6,140,500 | A | 10/2000 | Yan et al. |
| 6,150,097 | A | 11/2000 | Tyagi et al. |
| 6,191,278 | B1 | 2/2001 | Lee et al. |
| 6,329,144 | B1 | 12/2001 | Kubista et al. |
| 6,355,421 | B1 | 3/2002 | Coull et al. |
| 6,383,752 | B1 | 5/2002 | Agrawal et al. |
| 6,403,341 | B1 | 6/2002 | Barnes et al. |
| 6,485,901 | B1 | 11/2002 | Gildea et al. |
| 6,548,250 | B1 | 4/2003 | Sorge |
| 6,589,743 | B2 | 7/2003 | Sorge |
| 6,590,091 | B2 | 7/2003 | Albagli et al. |
| 6,593,091 | B2 | 7/2003 | Keys et al. |
| 6,596,490 | B2 | 7/2003 | Dattagupta |
| 6,649,349 | B2 | 11/2003 | Gildea et al. |
| 7,060,809 | B2 | 6/2006 | Wengel et al. |
| 8,486,626 | B2 | 7/2013 | Umansky et al. |
| 11,441,191 | B2 | 9/2022 | Di Fiore et al. |
| 12,139,766 | B2 | 11/2024 | Di Fiore et al. |
| 2006/0078894 | A1 | 4/2006 | Winkler et al. |
| 2009/0075258 | A1 | 3/2009 | Latham et al. |
| 2010/0010072 | A1 | 1/2010 | Dmitrovsky et al. |

(Continued)

FOREIGN PATENT DOCUMENTS

| | | | | |
|---|---|---|---|---|
| CA | 2793133 A1 * | 10/2011 | | C12Q 1/6886 |
| CN | 101284873 A | 10/2008 | | |

(Continued)

OTHER PUBLICATIONS

Yersal et al. World J Clin Oncol. 2014. 5(3):412-424. (Year: 2014).*
Chen. MCP Papers in Press. 2002. 10 pages. (Year: 2002).*
Cuzick et al. "Prognostic value of a combined estrogen receptor, progesterone receptor, Ki-67, and human epidermal growth factor receptor 2 immunohistochemical score and comparison with the Genomic Health recurrence score in early breast cancer", J Clin Oncol. Nov. 10, 2011; 29(32): 4273-8. doi:10.1200/JCO.2010.31.2835. Epub Oct. 11, 2011.
International Preliminary Report on Patentability issued in PCT/EP2021/062176, dated Nov. 8, 2022, 14 pages.
International Search Report and Written Opinion issued in PCT/EP2021/062176, dated Jul. 14, 2021, 17 pages.

(Continued)

*Primary Examiner* — Joseph G. Dauner
(74) *Attorney, Agent, or Firm* — Wolf, Greenfield & Sacks, P.C.

(57) ABSTRACT

The present invention relates to methods and kits for the evaluation of risk and treatment of distant recurrence of breast cancer in a subject. The methods and kits can comprise combining the measured expression levels of a subset of genes selected from a 20-gene signature with tumor size and nodal status to determine the risk of distant recurrence.

20 Claims, 5 Drawing Sheets

(56) References Cited

U.S. PATENT DOCUMENTS

| | | | | |
|---|---|---|---|---|
| 2011/0172928 | A1 | 7/2011 | Gehrmann et al. | |
| 2012/0225925 | A1 | 9/2012 | Sozzi et al. | |
| 2012/0309645 | A1 | 12/2012 | Keller et al. | |
| 2013/0035251 | A1 | 2/2013 | Keller et al. | |
| 2013/0184175 | A1 | 7/2013 | Beaudenon-Huibregtse et al. | |
| 2014/0018411 | A1 | 1/2014 | Croce et al. | |
| 2014/0031415 | A1 | 1/2014 | Brown et al. | |
| 2015/0191794 | A1 | 7/2015 | Sozzi et al. | |
| 2017/0204467 | A1 | 7/2017 | Sozzi et al. | |
| 2018/0216199 | A1 | 8/2018 | Cho et al. | |
| 2019/0119756 | A1 | 4/2019 | Sozzi et al. | |
| 2019/0161809 | A1* | 5/2019 | Di Fiore | C12Q 1/6886 |
| 2021/0301350 | A1 | 9/2021 | Sozzi et al. | |
| 2023/0151428 | A1 | 5/2023 | Di Fiore et al. | |
| 2025/0101532 | A1 | 3/2025 | Di Fiore et al. | |

FOREIGN PATENT DOCUMENTS

| | | | | |
|---|---|---|---|---|
| CN | 101804208 | A | 8/2010 | |
| EP | 3260553 | A1 * | 12/2017 | C12Q 1/6886 |
| WO | WO 1997/045539 | A1 | 12/1997 | |
| WO | WO 1999/021881 | A1 | 5/1999 | |
| WO | WO 2000/061612 | A2 | 10/2000 | |
| WO | WO 2007/081720 | A2 | 7/2007 | |
| WO | WO 2008/037700 | A2 | 4/2008 | |
| WO | WO 2009/052386 | A1 | 4/2009 | |
| WO | WO 2009/070653 | A1 | 6/2009 | |
| WO | WO 2009/147525 | A1 | 12/2009 | |
| WO | WO 2010/003771 | A1 | 1/2010 | |
| WO | WO 2010/099161 | A1 | 9/2010 | |
| WO | WO 2011/025919 | A1 | 3/2011 | |
| WO | WO 2011/053257 | A2 | 5/2011 | |
| WO | WO 2012/107841 | A2 | 8/2012 | |
| WO | WO 2013/063519 | A1 | 5/2013 | |
| WO | WO-2017096457 | A1 * | 6/2017 | G01N 33/57415 |
| WO | WO-2017220492 | A1 * | 12/2017 | C12Q 1/6886 |
| WO | WO-2021224466 | A1 | 11/2021 | |

OTHER PUBLICATIONS

Pece et al. “Integration of the stem cell biology-based genomic tool, StemPrintER, with clinicopathological parameters for the prediction of distant recurrence in ER+/HER2-breast cancer (BC) patients”, Journal of Clinical Oncology 38, No. 15_suppl (May 20, 2020) 1057-1057, DOI: 10.1200/JCO.2020.38.15_suppl.1057, XP055738768.

Sestak et al. “Comparison of the Performance of 6 Prognostic Signatures for Estrogen Receptor-Positive Breast Cancer: A Secondary Analysis of a Randomized Clinical Trial”, JAMA Oncol. Apr. 1, 2018; 4(4): 545-553. doi:10.1001/jamaoncol.2017.5524.

Zurrida et al. “A new TNM classification for breast cancer to meet the demands of the present and the challenges of the future”, Women’s Health (Lond). Jan. 2011; 7(1): 41-9. doi:10.2217/whe.10.82.

International Search Report and Written Opinion, mailed Apr. 20, 2015, for Application No. PCT/EP2014/079499 (5 pages).

International Preliminary Report on Patentability, mailed Jul. 14, 2016, for Application No. PCT/EP2014/079499 (9 pages).

International Search Report and Written Opinion, mailed Sep. 15, 2017, for Application No. PCT/EP2017/064937 (17 pages).

International Preliminary Report on Patentability, mailed Jan. 3, 2019, for Application No. PCT/EP2017/064937 (9 pages).

[No Author Listed] Agilent High-Resolution Microarray Scanner, Aug. 20, 2010, retrieved Aug. 26, 2011. www.chem.agilent.com/Library/datasheets/Public/5990-6404enlo.pdf, 2 pages.

[No Author Listed] Agilent Human, Mouse, and Rat miRNA Microarrays, Jan. 16, 2009, retrieved Aug. 26, 2011. www.chem.agilent.com/Library/brochures/5989-7688enlo.pdf, 4 pages.

Aberle et al., Reduced lung-cancer mortality with low-dose computed tomographic screening, N Engl J Med. Aug. 4, 2011; 365(5): 395-409. Epub Jun. 29, 2011.

Arroyo et al., Argonaute2 complexes carry a population of circulating microRNAs independent of vesicles in human plasma, Proc Natl Acad Sci US A. Mar. 22, 2011; 108(12): 5003-8. Epub Mar. 7, 2011.

Bach et al., Benefits and harms of CT screening for lung cancer: a systematic review, JAMA. Jun. 13, 2012; 307(22): 2418-29. Erratum in: JAMA. Oct. 3, 2012; 308(13):1324. Erratum in: JAMA. Jun. 5, 2013; 309(21): 2212. Author Manuscript, 25 pages.

Bach et al., Reduced lung-cancer mortality with CT screening, N Engl J Med. Nov. 24, 2011; 365(21): 2036; author reply 2037-8. doi: 10.1056/NEJMc1110293.

Barczak et al., UCSF 4Hs version 2 human long oligo array, Gene Expression, 2003, 397 pages. probes ID: HD200001112, H200005758, HD200007211.

Benner et al., Evolution, language and analogy in functional genomics. Trends Genet. Jul. 2001;17(7):414-8. doi: 10.1016/s0168-9525(01)02320-4.

Bianchi et al., A serum circulating miRNA diagnostic test to identify asymptomatic high-risk individuals with early stage lung cancer, EMBO Mol Med. Aug. 2011; 3(8): 495-503. Epub Jul. 11, 2011.

Boeri et al., MicroRNA signatures in tissues and plasma predict development and prognosis of computed tomography detected lung cancer. Proc Natl Acad Sci U S A. Mar. 1, 2011;108(9):3713-8. doi: 10.1073/pnas.1100048108. Epub Feb. 7, 2011. Supporting Information, 3 pages.

Boeri et al., Role of microRNAs in lung cancer: microRNA signatures in cancer prognosis. Cancer J. May-Jun. 2012;18(3):268-74. doi: 10.1097/PPO.0b013e318258b743.

Chen et al., Characterization of microRNAs in serum: a novel class of biomarkers for diagnosis of cancer and other diseases, Cell Res. Oct. 2008; 18(10): 997-1006.

Chen et al., Discordant protein and mRNA expression in lung adenocarcinomas. Mol Cell Proteomics. Apr. 2002;1(4):304-13. doi: 10.1074/mcp.m200008-mcp200.

Cheung et al., Natural variation in human gene expression assessed in lymphoblastoid cells. Nature Genetics, 33:422-425 (2003).

Cobb et al., Sepsis gene expression profiling: murine splenic compared with hepatic responses determined by using complementary DNA microarrays. Crit Care Med. Dec. 2002;30(12):2711-21. doi: 10.1097/00003246-200212000-00016.

De Guire et al., Circulating miRNAs as sensitive and specific biomarkers for the diagnosis and monitoring of human diseases: Promises and challenges, Clin Biochem. Jul. 2013; 46(10-11): 846-60. Epub Apr. 3, 2013.

Desmedt et al., Strong time dependence of the 76-gene prognostic signature for node-negative breast cancer patients in the TRANSBIG multicenter independent validation series. Clin Cancer Res. Jun. 1, 2007;13(11):3207-14. doi: 10.1158/1078-0432.CCR-06-2765.

Du et al., miR-93, miR-98, and miR-197 Regulate Expression of Tumor Suppressor Gene FUS1, Mol Cancer Res. Aug. 2009; 7(8): 1234-43. Epub Aug. 11, 2009.

Erdmann et al., Down-Regulation of Selected MicroRNAs Correlates With Expression of Prostate Cancer Associated Genes., (Abstract #1300), The Journal of Urology, Apr. 2010;183(4S):e503.

Gallo et al., The majority of microRNAs detectable in serum and saliva is concentrated in exosomes, PLoS One. 2012; 7(3): e30679. Epub Mar. 9, 2012.

Geffen et al., The impact of the 21-gene recurrence score assay on decision making about adjuvant chemotherapy in early-stage estrogen-receptor-positive breast cancer in an oncology practice with a unified treatment policy. Ann Oncol. Nov. 2011;22(11):2381-2386. doi: 10.1093/annonc/mdq769. Epub Mar. 1, 2011.

Goldhirsch et al., Personalizing the treatment of women with early breast cancer: highlights of the St Gallen International Expert Consensus on the Primary Therapy of Early Breast Cancer 2013. Ann Oncol. Sep. 2013;24(9):2206-23. doi: 10.1093/annonc/mdt303. Epub Aug. 4, 2013.

Goulart et al., Lung cancer screening with low-dose computed tomography: costs, national expenditures, and cost-effectiveness, J Natl Compr Cane Netw. Feb. 2012; 10(2): 267-75.

Haibe-Kains et al., Comparison of prognostic gene expression signatures for breast cancer. BMC Genomics. Aug. 21, 2008;9:394. doi: 10.1186/1471-2164-9-394.

Harrell et al., Multivariable prognostic models: issues in developing models, evaluating assumptions and adequacy, and measuring and reducing errors. Stat Med. Feb. 28, 1996;15(4):361-87. doi: 10.1002/(SICI)1097-0258(19960229)15:4<361::AID-SIM168>3.0.CO;2-4.

(56) References Cited

OTHER PUBLICATIONS

Heagerty et al., Time-dependent ROC curves for censored survival data and a diagnostic marker, Biometrics. Jun. 2000; 56(2): 337-44.
Hoshikawa et al. Hypoxia induces different genes in the lungs of rats compared with mice. Physiol Genomics. Feb. 6, 2003;12(3):209-19. doi: 10.1152/physiolgenomics.00081.2001.
Huang et al., Identification of Gene Expression Pattern Related to Breast Cancer Survival Using Integrated TCGA Datasets and Genomic Tools. Biomed Res Int. 2015;2015:878546. doi: 10.1155/2015/878546. Epub Oct. 20, 2015.
Infante et al., A randomized study of lung cancer screening with spiral computed tomography: three-year results from the DANTE trial, Am J Respir Grit Care Med. Sep. 1, 2009; 180(5): 445-53. Epub Jun. 11, 2009.
Iorio et al., MicroRNA dysregulation in cancer: diagnostics, monitoring and therapeutics. A comprehensive review, EMBO Mol Med. Mar. 2012; 4(3):143-59. Epub Feb. 20, 2012.
Ivshina et al., Genetic reclassification of histologic grade delineates new clinical subtypes of breast cancer. Cancer Res. Nov. 1, 2006;66(21):10292-301. doi: 10.1158/0008-5472.CAN-05-4414.
Jemal et al., Global cancer statistics. CA Cancer J Clin. Mar.-Apr. 2011;61(2):69-90. doi: 10.3322/caac.20107. Epub Feb. 4, 2011. Erratum in: CA Cancer J Clin. Mar.-Apr. 2011;61(2):134.
Karkera et al., The mirR-21 :miR-221 Ratio as a Serum-Based Diagnostic for Non-Small Cell Lung Cancer, (Abstract#3015), AACR 101st Annual Meeting 2010, Apr. 20, 2010, 1 page.
Karlsson et al., The mTOR effectors 4EBP1 and S6K2 are frequently coexpressed, and associated with a poor prognosis and endocrine resistance in breast cancer: a retrospective study including patients from the randomised Stockholm tamoxifen trials. Breast Cancer Res. 2013;15(5):R96. doi: 10.1186/bcr3557.
Kirschner et al., Haemolysis during sample preparation alters microRNA content of plasma. PLoS One. 2011;6(9):e24145. doi: 10.1371/journal.pone.0024145. Epub Sep. 1, 2011.
Lam et al., EarlyCDT-Lung: an immunobiomarker test as an aid to early detection of lung cancer. Cancer Prev Res (Phila). Jul. 2011;4(7):1126-34. doi: 10.1158/1940-6207.CAPR-10-0328.
Li et al., Antiprimer Quenching-Based Real-Time PCR and Its Application to the Analysis of Clinical Cancer Samples, Clin Chem. Apr. 2006; 52(4): 624-33. Epub Feb. 9, 2006.
Liang et al., Characterization of microRNA expression profiles in normal human tissues. BMC Genomics. Jun. 12, 2007;8:166. doi: 10.1186/1471-2164-8-166.
Liang, An expression meta-analysis of predicted microRNA targets identifies a diagnostic signature for lung cancer. BMC Med Genomics. Dec. 16, 2008;1:61. doi: 10.1186/1755-8794-1-61.
Loi et al., Predicting prognosis using molecular profiling in estrogen receptor-positive breast cancer treated with tamoxifen. BMC Genomics. May 22, 2008;9:239. doi: 10.1186/1471-2164-9-239.
Meder et al., MicroRNA signatures in total peripheral blood as novel biomarkers for acute myocardial infarction, Basic Res Cardiol. Jan. 2011; 106(1): 13-23. Epub Oct. 1, 2010.
Mitchell et al., Circulating microRNAs as stable blood-based markers for cancer detection. Proc Natl Acad Sci U S A. Jul. 29, 2008;105(30):10513-8. doi: 10.1073/pnas.0804549105. Epub Jul. 28, 2008.
Neely et al., A microRNA expression ratio defining the invasive phenotype in bladder tumors. Urol Oncol. Jan.-Feb. 2010;28(1):39-48. doi: 10.1016/j.urolonc.2008.06.006. Epub Sep. 16, 2008.
Paik et al., A multigene assay to predict recurrence of tamoxifen-treated, node-negative breast cancer. N Engl J Med. Dec. 30, 2004;351(27):2817-26. doi: 10.1056/NEJMoa041588. Epub Dec. 10, 2004.
Pastorino et al., Annual or biennial CT screening versus observation in heavy smokers: 5-year results of the MILD trial. Eur J Cancer Prev. May 2012; 21(3): 308-15.
Pawitan et al., Gene expression profiling spares early breast cancer patients from adjuvant therapy: derived and validated in two population-based cohorts. Breast Cancer Res. 2005;7(6):R953-64. doi: 10.1186/bcr1325. Epub Oct. 3, 2005.
Pece et al., Biological and molecular heterogeneity of breast cancers correlates with their cancer stem cell content. Cell. Jan. 8, 2010;140(1):62-73. doi: 10.1016/j.cell.2009.12.007.
Pepe et al., Phases of Biomarker Development for Early Detection of Cancer, J Natl Cancer Inst. Jul. 18, 2001; 93(14): 1054-61. doi: 10.1093/jnci/93.14.1054.
Peres et al., Lung cancer screening gets risk-specific, J Natl Cancer Inst. Jan. 2, 2013; 105(1): 1-2. Epub Dec. 20, 2012.
Pizzamiglio et al., A methodological procedure for evaluating the impact of hemolysis on circulating microRNAs. Oncol Lett. Jan. 2017;13(1):315-320. doi: 10.3892/ol.2016.5452. Epub Nov. 30, 2016.
Pritchard et al., Blood cell origin of circulating microRNAs: a cautionary note for cancer biomarker studies. Cancer Prev Res (Phila). Mar. 2012;5(3):492-497. doi: 10.1158/1940-6207.CAPR-11-0370. Epub Dec. 12, 2011.
Qi et al., MicroRNAs and lung cancers: from pathogenesis to clinical implications, Front Med. Jun. 2012; 6(2): 134-55. Epub Apr. 18, 2012. Author Manuscript, 36 pages.
Qian et al., MicroRNA expression profile of bronchioalveolar stem cells from mouse lung, Biochem Biophys Res Commun. Dec. 12, 2008; 377(2): 668-673. Epub Oct. 21, 2008.
Raponi et al., MicroRNA classifiers for predicting prognosis of squamous cell lung cancer. Cancer Res. Jul. 15, 2009;69(14):5776-83. doi: 10.1158/0008-5472.CAN-09-0587. Epub Jul. 7, 2009.
Rodriguez-Dorantes et al., Prostate Cancer Detection Using a Noninvasive Method for Quantifying miRNAs, Methods Mol Biol. 2014; 1165:81-7.
Saghir et al., CT screening for lung cancer brings forward early disease. The randomised Danish Lung Cancer Screening Trial: status after five annual screening rounds with low-dose CT Thorax. Apr. 2012; 67(4): 296-301. Epub Jan. 27, 2012.
Schouten et al., Relative quantification of 40 nucleic acid sequences by multiplex ligation-dependent probe amplification. Nucleic Acids Res. Jun. 15, 2002;30(12):e57. doi: 10.1093/nar/gnf056.
Sorlie et al., Gene expression patterns of breast carcinomas distinguish tumor subclasses with clinical implications. Proc Natl Acad Sci U S A. Sep. 11, 2001;98(19):10869-74. doi: 10.1073/pnas.191367098.
Sotiriou et al., Gene expression profiling in breast cancer: understanding the molecular basis of histologic grade to improve prognosis. J Natl Cancer Inst. Feb. 15, 2006;98(4):262-72. doi: 10.1093/jnci/djj052.
Sozzi et al., MicroRNA expression profile of CT screening detected lung cancer. Cancer Research. Apr. 15, 2010;70(8_Supplement):3021.
Sparano et al., TOP2A RNA expression and recurrence in estrogen receptor-positive breast cancer. Breast Cancer Res Treat. Jul. 2012;134(2):751-7. doi: 10.1007/s10549-012-2112-7. Epub Jun. 16, 2012. Author Manuscript, 12 pages.
Tanaka et al., Down-regulation of miR-92 in human plasma is a novel marker for acute leukemia patients. PLoS One. 2009;4(5):e5532. doi: 10.1371/journal.pone.0005532. Epub May 14, 2009.
Turchinovich et al., Characterization of extracellular circulating microRNA. Nucleic Acids Res. Sep. 1, 2011; 39(16): 7223-33. Epub May 24, 2011.
Van Wieringen et al., Survival prediction using gene expression data: A review and comparison, Computational Statistics & Data Analysis, 2009, vol. 53, p. 1590-1603.
Vant Veer et al., Gene expression profiling predicts clinical outcome of breast cancer. Nature. Jan. 31, 2002;415(6871):530-6. doi: 10.1038/415530a.
Waldron et al., Optimized application of penalized regression methods to diverse genomic data. Bioinformatics. Dec. 15, 2011;27(24):3399-406. doi: 10.1093/bioinformatics/btr591.
Wang et al., Gene-expression profiles to predict distant metastasis of lymph-node-negative primary breast cancer. Lancet. Feb. 19-25, 2005;365(9460):671-9. doi: 10.1016/S0140-6736(05)17947-1.
Wang et al., Plasma microRNA-133a is a new marker for both acute myocardial infarction and underlying coronary artery stenosis. J Transl Med. Sep. 23, 2013;11:222. doi: 10.1186/1479-5876-11-222.

(56) References Cited

OTHER PUBLICATIONS

Wang et al., Potential Uses of MicroRNA in Lung Cancer Diagnosis, Prognosis, and Therapy, Curr Cancer Drug Targets. Jun. 2009; 9(4): 572-94.
Weber et al., The microRNA spectrum in 12 body fluids. Clin Chem. Nov. 2010;56(11):1733-41. doi: 10.1373/clinchem.2010.147405. Epub Sep. 16, 2010.
Yanaihara et al., Unique microRNA molecular profiles in lung cancer diagnosis and prognosis. Cancer Cell. Mar. 2006;9(3):189-98. doi: 10.1016/j.ccr.2006.01.025.
Yang et al., Microvesicles secreted by macrophages shuttle invasion-potentiating microRNAs into breast cancer cells, Mol Cancer. Sep. 22, 2011; 10:117.
Yersal et al., Biological subtypes of breast cancer: Prognostic and therapeutic implications. World J Clin Oncol. Aug. 10, 2014;5(3):412-24. doi: 10.5306/wjco.v5.i3.412.
Zheng et al., Prospective accuracy for longitudinal markers. Biometrics. Jun. 2007;63(2):332-41. doi: 10.1111/j.1541-0420.2006.00726.x.
Zhou et al., Detection of circulating tumor cells in peripheral blood from patients with gastric cancer using microRNA as a marker. J Mol Med (Berl). Jul. 2010;88(7):709-17. doi: 10.1007/s00109-010-0617-2. Epub Mar. 28, 2010.

* cited by examiner

METHODS AND KITS FOR DETERMINING THE RISK OF BREAST CANCER RECURRENCE

CROSS-REFERENCE TO RELATED APPLICATIONS

This application is a U.S. National Phase application, filed under 35 U.S.C. § 371, of International Application No. PCT/EP2021/062176, filed May 7, 2021, which claims the benefit of priority to E.P. application No. 20173612.1, filed May 8, 2020, the contents of each of which are incorporated by reference herein in their entireties.

FIELD OF THE INVENTION

This disclosure relates generally to the field of breast cancer biology, and specifically, to refined prognostic clinical tools, methods, and kits for the evaluation of risk and management of distant recurrence in ER+/HER2− breast cancer patients.

BACKGROUND OF THE INVENTION

Endocrine receptor-positive (ER+)/HER2-negative (HER2−) breast cancers constitute the majority (approximately >75%) of breast cancer cases. Due to the high level of molecular and clinical heterogeneity displayed by these cancers, prognosis and therapy response are often difficult to predict. This makes the clinical management of the ER+/HER2− breast cancer patients challenging, particularly, in terms of the type and the duration of the adjuvant systemic therapy an individual should receive. Based on the intrinsic risk of recurrence (typically assessed using standard clinico-pathological parameters), ER+/HER2− breast cancer patients may be offered adjuvant chemotherapy in addition to hormonal therapy or prolonged hormonal therapy beyond the five years standard of care. However, since standard clinico-pathological parameters are often insufficient to accurately predict risk of recurrence in these patients, a significant proportion of patients are, consequently, either over- or under-treated.

Accordingly, an unmet need exists for more refined prognostic clinical tools for the evaluation of risk and management of distant recurrence in ER+/HER2− breast cancer patients.

SUMMARY OF THE INVENTION

The present disclosure provides a method for predicting a risk of breast cancer recurrence in a subject having at least one breast cancer tumor, the method comprising: (a) determining, in a sample from the subject, the expression level of at least one gene from Table 1; (b) determining the tumor size (pT) of the at least one breast cancer tumor; (c) determining the nodal status (pN) of the at least one breast cancer tumor; and (d) calculating a risk score based upon the expression level of the at least one gene, the pT and the pN.

The present disclosure also provides a method for stratifying a subject having at least one breast cancer tumor into a low or high risk group of breast cancer recurrence, the method comprising: (a) determining, in a sample from the subject, the expression level of at least one gene from Table 1; (b) determining the tumor size (pT) of the at least one breast cancer tumor; (c) determining the nodal status (pN) of the at least one breast cancer tumor; (d) calculating a risk score based upon the expression level of the at least one gene, the pT and the pN; and (e) stratifying the subject based upon the calculated risk score.

The present disclosure also provides a method for stratifying a subject having at least one breast cancer tumor into a low, intermediate, or high risk group of breast cancer recurrence, the method comprising: (a) determining, in a sample from the subject, the expression level of at least one gene from Table 1; (b) determining the tumor size (pT) of the at least one breast cancer tumor; (c) determining the nodal status (pN) of the at least one breast cancer tumor; (d) calculating a risk score based upon the expression level of the at least one gene, the pT and the pN; and (e) stratifying the subject based upon the calculated risk score.

In some aspects of the preceding methods, step (a) can comprise determining, in a sample from the subject, the expression level of each of the twenty genes from Table 1.

In some aspects of the preceding methods, step (d) can comprise determining a risk score based upon the expression level of each of the twenty genes, the pT and the pN.

In some aspects of the preceding methods, step (a) can comprise determining, in a sample from the subject, the expression level of at least three genes from Table 1, wherein the at least three genes: a) comprises at least EIF4EBP1, MRPS23, and TOP2A; or b) consist of EIF4EBP1, MRPS23, and TOP2A.

In some aspects of the preceding methods, step (a) can comprise determining, in a sample from the subject, the expression level of at least nine genes from Table 1, wherein the at least nine genes: a) comprises at least APOBEC3B, CENPW, EIF4EBP1, EXOSC4, LY6E, MMP1, MRPS23, NDUFB10, and TOP2A; or b) consist of APOBEC3B, CENPW, EIF4EBP1, EXOSC4, LY6E, MMP1, MRPS23, NDUFB10, and TOP2A.

In some aspects of the preceding methods, step (a) can comprise determining, in a sample from the subject, the expression level of at least sixteen genes from Table 1, wherein the at least sixteen genes: a) comprises at least ALYREF, APOBEC3B, CDK1, CENPW, EIF4EBP1, EXOSC4, H2AFJ, LY6E, MIEN1, MMP1, MRPS23, NDUFB10, NOL3, RACGAP1, SFN, and TOP2A; or b) consist of ALYREF, APOBEC3B, CDK1, CENPW, EIF4EBP1, EXOSC4, H2AFJ, LY6E, MIEN1, MMP1, MRPS23, NDUFB10, NOL3, RACGAP1, SFN, and TOP2A.

In some aspects of the preceding methods, step (d) can comprise determining a risk score based upon the expression level of the at least three, or the at least nine, or the at least sixteen genes, the pT and the pN.

In some aspects of the preceding methods, stratifying a subject based upon the calculated risk score can comprise stratifying the subject as having a low risk for breast cancer recurrence when the risk score is less than a predetermined cutoff value. In some aspects of the preceding methods, a predetermined cutoff value can be 49.

In some aspects of the preceding methods, stratifying a subject based upon the calculated risk score can comprise stratifying the subject as having a high risk for breast cancer recurrence when the risk score is greater than a predetermined cutoff value. In some aspects of the preceding methods, a predetermined cutoff value can be 59.

In some aspects of the preceding methods, stratifying a subject based upon the calculated risk score can comprise stratifying the subject as having an intermediate risk for breast cancer recurrence when the risk score is greater than or equal to a first predetermined cutoff value and less than or equal to a second predetermined cutoff value. In some aspects of the preceding methods, a first predetermined cutoff value can be 49 and the second predetermined cutoff value can be 59.

In some aspects of the preceding methods, the method can further comprise administering at least one treatment to the subject based on the risk score.

In some aspects of the preceding methods, the method can further comprise administering to the subject stratified as having a high risk of breast cancer recurrence a cancer treatment that is more aggressive than a cancer treatment provided to a subject stratified as having a low risk of breast cancer recurrence.

In some aspects of the preceding methods, the method can further comprise administering to the subject stratified as having a high risk of breast cancer recurrence a cancer treatment that is more aggressive than a cancer treatment provided to a subject stratified as having an intermediate risk of breast cancer recurrence.

In some aspects of the preceding methods, the method can further comprise administering to the subject stratified as having an intermediate risk of breast cancer recurrence a cancer treatment that is more aggressive than a cancer treatment provided to a subject stratified as having a low risk of breast cancer recurrence.

In some aspects of the preceding methods, an at least one treatment can comprise adjuvant chemotherapy.

In some aspects of the preceding methods, a more aggressive treatment can comprise adjuvant chemotherapy.

In some aspects of the preceding methods, a risk score can be calculated according to the following formula:

$$\text{Risk Score} = \frac{(0.03604)\times\left(\sum_i \beta_i \times Cq_{normalized}\right) + pT + pN}{5.64032}$$

wherein i is the summation index for the genes for which the expression level was measured;

β is the ridge penalized Cox model coefficient for each gene as put forth in Table 1, Table 2, Table 3 or Table 4; and $Cq_{normalized}$ is the normalized average Cq for each of the genes for which the expression level was measured;

wherein pT is 0.45542 if the tumor size of the at least one breast cancer tumor is determined to be pT1c; or pT is 0.96572 if the tumor size of the breast cancer tumor is determined to be any of pT2, pT3 and pT4; and wherein pN is 0.46293 if the nodal status of the at least one breast cancer tumor is determined to be pN1; or pN is 1.24922 if the nodal status of the at least one breast cancer tumor is determined to be pN2.

In some aspects of the preceding methods, Cqnormalized can be normalized to the expression of at least one reference gene. An at least one reference gene can be a housekeeping gene. An at least one reference gene can be selected from the group consisting of GAPDH, GUSB, HPRT1, and TBP. An at least one reference gene can comprise at least each of GAPDH, GUSB, HPRT1, and TBP.

In some aspects of the preceding methods, $Cq_{normalized}$ can be calculated according to the following formula:

$$Cq_{normalized} = AVG\ Cq - SF$$

wherein SF is the difference between the AVG Cq value of the at least one reference gene for each subject and a constant reference value K.

In some aspects of the preceding methods, K can be the mean of the AVG Cq of the at least one reference gene calculated across a plurality of training samples. In some aspects, K can be 25.012586069.

In some aspects of the preceding methods, gene expression can be determined using one or more techniques selected from the group consisting of analysis of single strand conformation polymorphism, capillary electrophoresis, denaturing high performance liquid chromatography, digital molecular barcoding technology, e.g., NANOSTRING® nCounter® system, direct sequencing, DNA mismatch-binding protein assays, dynamic allele-specific hybridization, Fluorescent in situ hybridization (FISH), high-density oligonucleotide SNP arrays, high-resolution melting analysis, microarray, next generation sequencing (NGS), e.g., using the ILLUMINA® Genome Analyzer, ABI Solid instrument, ROCHE® 454 instrument, Heliscope instrument, Northern blot analysis, nuclease protection analysis, oligonucleotide ligase assays, polymerase chain reaction (PCR), primer extension assays, QUANTIGENE® analysis, quantitative nuclease-protection assay (qNPA), reporter gene detection, restriction fragment length polymorphism (RFLP) assays, reverse transcription and real-time quantitative polymerase chain reaction (RT-qPCR), reverse transcription-polymerase chain reaction (RT-PCR), RNA sequencing (RNA-seq), Serial analysis of gene expression (SAGE), Single Molecule Real Time (SMRT) DNA sequencing technology, SNPLex, Southern blot analysis, SYBR® Green chemistry, TAQMAN®-based assays, temperature gradient gel electrophoresis (TGGE), Tiling array, Western blot analysis, and immunohistochemistry.

In some aspects of the preceding methods, gene expression can be determined using reverse transcription and real-time quantitative polymerase chain reaction (RT-qPCR).

In some aspects of the preceding methods, gene expression can be determined using microarray analysis.

In some aspects of the preceding methods, a sample can be a tumor obtained from the subject, a cancerous cell obtained from the subject, or a cancer stem cell obtained from the subject; or wherein the sample is a primary cell line derived from a tumor obtained from the subject, from a cancerous cell obtained from the subject, or from a cancer stem cell obtained from the subject.

In some aspects of the preceding methods, a subject can have a ER+/HER2− breast cancer.

The present disclosure provides a kit for use in the methods of the present disclosure. A kit can comprise comprising reagents sufficient for determining the expression levels of the at least one, at least three, at least nine, at least sixteen or each of the twenty genes from Table 1.

In some aspects, the disclosure provides a method for treating a breast cancer in a subject in need thereof, the method comprising the steps of: (a) predicting a risk of breast cancer recurrence in the subject; or (b) stratifying the subject into a low or high risk group of breast cancer recurrence; and (c) administering a treatment to the subject, wherein the treatment is based on (a) or (b). In some embodiments, predicting a risk of breast cancer recurrence in the subject comprises the methods described herein. In some embodiments, stratifying the subject into a low or high risk group of breast cancer recurrence comprises the methods described herein. In some embodiments, the breast cancer is ER+/HER2− breast cancer. In some embodiments, the treatment is a breast cancer treatment. In some embodiments, the breast cancer treatment comprises surgery, radiation, anthracycline agents, alkylating agents, nucleoside analogs, platinum agents, vinca agents, anti-estrogen drugs, aromatase inhibitors, ovarian suppression agents, endocrine/hormonal agents, bisphophonate therapy agents and targeted biological therapy agents (e.g., antibodies), or combinations thereof. In some embodiments, the breast cancer treatment comprises cyclophosphamide, fluorouracil (or 5-fluorouracil or 5-FU), methotrexate, thiotepa, carboplatin, cisplatin, gemcitabine, anthracycline, taxanes, paclitaxel, protein-bound paclitaxel, doxorubicin, docetaxel, vinorelbine, tamoxifen, raloxifene, toremifene, fulvestrant, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

DETAILED DESCRIPTION OF THE INVENTION

Figure 1:
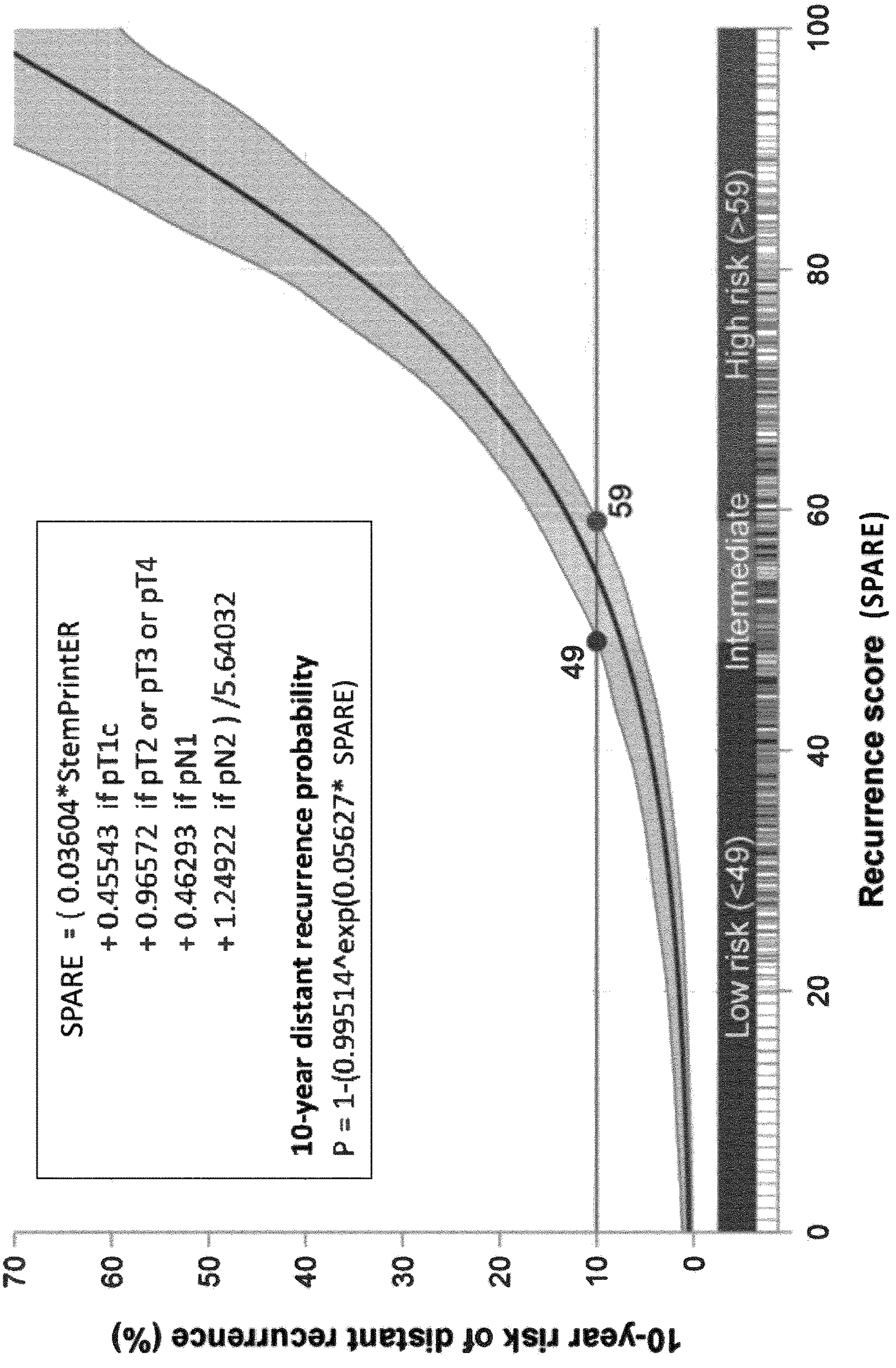
FIG. 1 is a graph showing the 10-year risk of distant recurrence (%) vs. the recurrence score as calculated using the SPARE methods of the present disclosure.

The present invention relates to improved prognostic clinical tools, methods, and kits for the evaluation of risk and management of distant recurrence in ER+/HER2− breast cancer patients. The present invention also relates to improved methods of treating ER+/HER2− breast cancer patients with the risk of distant recurrence.

The present invention is based in part through a retrospective analysis of a consecutive cohort of 1,827 ER+/HER2− breast cancer patients with long-term follow-up (~15 years). The retrospective analysis yielded a 20-gene signature (and subsets thereof) that is, in combination with the tumor size (pT) and nodal status (pN), able to stratify breast cancer patients according to risk of early and late recurrence. The methods of the present disclosure, herein referred to as the StemPrintER risk score (SPRS) for Personalized Adjuvant therapy in Receptor-Expressing patients (SPARE) methods, function as prognostic-predictive clinical tools in ER+/HER2− breast cancer patients that may be used to guide clinical decision-making on the selection of adjuvant systemic therapies. The 20-gene signature can be further partitioned into 3, 9, 16, and 20-gene signatures, i.e., the "StemPrintER3 genomic predictor", "StemPrintER5 genomic predictor", "StemPrintER9 genomic predictor", "StemPrintER16 genomic predictor", and "StemPrintER20 genomic predictor", which, in combination with the tumor size (pT) and nodal status (pN) can function as prognostic-predictive clinical tools in ER+/HER2− breast cancer patients that may be used to guide clinical decision-making on the selection of adjuvant systemic therapies.

The StemPrintER risk score, StemPrintER3 genomic predictor, StemPrintER9 genomic predictor, StemPrintER16 genomic predictor, and StemPrintER20 genomic predictor are described in further detail in US Patent Application Publication No. 2019-0161809 and International Patent Application Publication No. WO2017/220492, both of which are incorporated by reference in their entireties. The present disclosure is based in part on the surprising and unexpected finding that combining any of the StemPrintER risk score, StemPrintER3 genomic predictor, StemPrintER9 genomic predictor StemPrintER16 genomic predictor, and StemPrintER20 genomic predictor with clinicopathological parameters including, but not limited to, the subject's tumor size (pT) and nodal status (pN) provides a more accurate and powerful prognostic tool that can be used, for example, in personalized therapeutic decision making in ER+/HER2− breast cancer patients. In fact, the methods of the present disclosure outperform the Clinical Treatment Score (CTS) algorithm, which is widely accepted in the field as one of the most powerful predictive algorithms for distant recurrence of breast cancer. Methods for deriving the CTS are well known in the art (see Cuzick J, et al., J Clin Oncol. 2011; 29 (32): 4273-4278).

The present disclosure provides a method of predicting a risk of breast cancer recurrence in a subject having at least one breast cancer tumor, the method comprising: (a) determining, in a sample from the subject, the expression level of at least one gene from Table 1; (b) determining the tumor size (pT) of the at least one breast cancer tumor; (c) determining the nodal status (pN) of the at least one breast cancer tumor; and (d) calculating a risk score based upon the expression level of the at least one gene, the pT and the pN.

The present disclosure provides a method of stratifying a subject having at least one breast cancer tumor into a low or high risk group for breast cancer recurrence, the method comprising: (a) determining, in a sample from the subject, the expression level of at least one gene from Table 1; (b) determining the tumor size (pT) of the at least one breast cancer tumor; (c) determining the nodal status (pN) of the at least one breast cancer tumor; (d) calculating a risk score based upon the expression level of the at least one gene, the pT and the pN; and (e) stratifying the subject based upon the calculated risk score.

The present disclosure provides a method of stratifying a subject having at least one breast cancer tumor into a low, intermediate or high risk group for breast cancer recurrence, the method comprising: (a) determining, in a sample from the subject, the expression level of at least one gene from Table 1; (b) determining the tumor size (pT) of the at least one breast cancer tumor; (c) determining the nodal status (pN) of the at least one breast cancer tumor; (d) calculating a risk score based upon the expression level of the at least one gene, the pT and the pN; and (e) stratifying the subject based upon the calculated risk score.

The present disclosure provides a method of stratifying a subject having at least one breast cancer tumor according to risk of breast cancer recurrence, the method comprising: (a) determining, in a sample from the subject, the expression level of at least one gene from Table 1; (b) determining the tumor size (pT) of the at least one breast cancer tumor; (c) determining the nodal status (pN) of the at least one breast cancer tumor; (d) calculating a risk score based upon the expression level of the at least one gene, the pT and the pN; and (e) stratifying the subject based upon the calculated risk score.

The present disclosure provides a method of treating breast cancer in a subject having at least one breast cancer tumor, the method comprising: (a) determining, in a sample from the subject, the expression level of at least one gene from Table 1; (b) determining the tumor size (pT) of the at least one breast cancer tumor; (c) determining the nodal status (pN) of the at least one breast cancer tumor; (d) calculating a risk score based upon the expression level of the at least one gene, the pT and the pN; and (e) administering at least one treatment based on the calculated risk score.

In some aspects of any of the preceding methods, step (a) can comprise determining, in a sample from the subject, the expression level of at least two, or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen genes from Table 1. Accordingly, calculating the risk score can comprise calculating a risk score based upon the expression level of the at least two, or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen genes, the pT and the pN.

In some aspects of any of the preceding methods, step (a) can comprise determining, in a sample from the subject, the expression level of each of the twenty genes from Table 1. Accordingly, calculating the risk score can comprise calculating a risk score based upon the expression level of the each of the twenty genes, the pT and the pN.

TABLE 1

| Gene | Ridge penalized Cox model coefficient (β) |
|---|---|
| H2AFZ | −0.03833591325196550 |
| CDK1 | −0.06132455806571770 |
| EXOSC4 | −0.02105976326055420 |
| PHLDA2 | −0.06295739658169650 |
| APOBEC3B | 0.02341881674020150 |
| EIF4EBP1 | −0.13911217901125500 |
| SFN | 0.05788269046891110 |
| PHB | −0.03538557745953510 |
| EPB41L5 | −0.04675539403890050 |
| RACGAP1 | −0.05097505893853430 |
| MRPS23 | −0.14201022110072700 |
| TOP2A | −0.11290078348786600 |
| H2AFJ | −0.04975471358452700 |
| NOL3 | −0.04193802459521500 |
| MIEN1 | 0.01133668644106850 |
| CENPW | −0.03717918353187610 |
| LY6E | −0.02829256296234230 |
| ALYREF | −0.09541915699494330 |
| MMP1 | −0.00911370427072023 |
| NDUFB10 | 0.00626166874136819 |

The present disclosure provides a method of predicting a risk of breast cancer recurrence in a subject having at least one breast cancer tumor, the method comprising: (a) determining, in a sample from the subject, the expression level of at least three genes from Table 1, wherein the at least three genes comprise at least EIF4EBP1, MRPS23, and TOP2A; (b) determining the tumor size (pT) of the at least one breast cancer tumor; (c) determining the nodal status (pN) of the at least one breast cancer tumor; and (d) calculating a risk score based upon the expression level of the at least three genes, the pT and the pN.

The present disclosure provides a method of stratifying a subject having at least one breast cancer tumor into a low or high risk group for breast cancer recurrence, the method comprising: (a) determining, in a sample from the subject, the expression level of at least three genes from Table 1, wherein the at least three genes comprise at least EIF4EBP1, MRPS23, and TOP2A; (b) determining the tumor size (pT) of the at least one breast cancer tumor; (c) determining the nodal status (pN) of the at least one breast cancer tumor; (d) calculating a risk score based upon the expression level of the at least three genes, the pT and the pN; and (e) stratifying the subject based upon the calculated risk score.

The present disclosure provides a method of stratifying a subject having at least one breast cancer tumor into a low, intermediate or high risk group for breast cancer recurrence, the method comprising: (a) determining, in a sample from the subject, the expression level of at least three genes from Table 1, wherein the at least three genes comprise at least EIF4EBP1, MRPS23, and TOP2A; (b) determining the tumor size (pT) of the at least one breast cancer tumor; (c) determining the nodal status (pN) of the at least one breast cancer tumor; (d) calculating a risk score based upon the expression level of the at least three genes, the pT and the pN; and (e) stratifying the subject based upon the calculated risk score.

The present disclosure provides a method of stratifying a subject having at least one breast cancer tumor according to risk of breast cancer recurrence, the method comprising: (a) determining, in a sample from the subject, the expression level of at least three genes from Table 1, wherein the at least three genes comprise at least EIF4EBP1, MRPS23, and TOP2A; (b) determining the tumor size (pT) of the at least one breast cancer tumor; (c) determining the nodal status (pN) of the at least one breast cancer tumor; (d) calculating a risk score based upon the expression level of the at least three genes, the pT and the pN; and (e) stratifying the subject based upon the calculated risk score.

The present disclosure provides a method of treating breast cancer in a subject having at least one breast cancer tumor, the method comprising: (a) determining, in a sample from the subject, the expression level of at least three genes from Table 1, wherein the at least three genes comprise at least EIF4EBP1, MRPS23, and TOP2A; (b) determining the tumor size (pT) of the at least one breast cancer tumor; (c) determining the nodal status (pN) of the at least one breast cancer tumor; (d) calculating a risk score based upon the expression level of the at least three genes, the pT and the pN; and (e) administering at least one treatment based on the calculated risk score.

In some aspects, the at least three genes can comprise at least EIF4EBP1, MRPS23, and TOP2A. In some aspects, the at least three genes can comprise at least APOBEC3B, CENPW, EIF4EBP1, EXOSC4, LY6E, MMP1, MRPS23, NDUFB10, and TOP2A. In some aspects, the at least three genes can comprise at least ALYREF, APOBEC3B, CDK1, CENPW, EIF4EBP1, EXOSC4, H2AFJ, LY6E, MIEN1, MMP1, MRPS23, NDUFB10, NOL3, RACGAP1, SFN, and TOP2A.

In some aspects, the at least three genes can consist of EIF4EBP1, MRPS23, and TOP2A. In some aspects, the at least three genes can consist of APOBEC3B, CENPW, EIF4EBP1, EXOSC4, LY6E, MMP1, MRPS23, NDUFB10, and TOP2A. In some aspects, the at least three genes can consist of ALYREF, APOBEC3B, CDK1, CENPW, EIF4EBP1, EXOSC4, H2AFJ, LY6E, MIEN1, MMP1, MRPS23, NDUFB10, NOL3, RACGAP1, SFN, and TOP2A.

In aspects wherein the at least three genes comprise at least EIF4EBP1, MRPS23, and TOP2A or consist of EIF4EBP1, MRPS23, and TOP2A, the ridge penalized Cox model coefficient for each gene (8) can be the coefficients put forth in Table 2.

TABLE 2

| Gene | Ridge penalized Cox model coefficient (β) |
|---|---|
| EIF4EBP1 | −0.2661522777700890 |
| MRPS23 | −0.4064807990811070 |
| TOP2A | −0.1898759903565910 |

In aspects wherein the at least three genes comprise at least APOBEC3B, CENPW, EIF4EBP1, EXOSC4, LY6E, MMP1, MRPS23, NDUFB10, and TOP2A or consist of APOBEC3B, CENPW, EIF4EBP1, EXOSC4, LY6E, MMP1, MRPS23, NDUFB10, and TOP2A, the ridge penalized Cox model coefficients for each gene (B) can be the coefficient put forth in Table 3.

TABLE 3

| Gene | Ridge penalized Cox model coefficient (β) |
|---|---|
| EXOSC4 | 0.3440660812818810 |
| APOBEC3B | 0.2110001016524630 |
| EIF4EBP1 | −0.2223133616036320 |
| MRPS23 | −0.4788624802373240 |
| TOP2A | −0.2406479942640310 |
| CENPW | −0.2053740290368180 |
| LY6E | −0.2897586785096140 |
| MMP1 | −0.0824402740633608 |
| NDUFB10 | 0.3085837868590590 |

In aspects wherein the at least three genes comprise at least ALYREF, APOBEC3B, CDK1, CENPW, EIF4EBP1, EXOSC4, H2AFJ, LY6E, MIEN1, MMP1, MRPS23, NDUFB10, NOL3, RACGAP1, SFN, and TOP2A or consist of ALYREF, APOBEC3B, CDK1, CENPW, EIF4EBP1, EXOSC4, H2AFJ, LY6E, MIEN1, MMP1, MRPS23, NDUFB10, NOL3, RACGAP1, SFN, and TOP2A, the ridge penalized Cox model coefficient for each gene (B) can be the coefficients put forth in Table 4.

TABLE 4

| Gene | Ridge penalized Cox model coefficient (β) |
|---|---|
| CDK1 | −0.0777226352877493 |
| EXOSC4 | 0.2571414958102690 |
| APOBEC3B | 0.2027825590936980 |
| EIF4EBP1 | −0.2329055344285050 |
| SFN | 0.0591955291393095 |
| RACGAP1 | −0.0928937254771330 |
| MRPS23 | −0.4265118770613120 |
| TOP2A | −0.1515759123771920 |
| H2AFJ | −0.0432973988579006 |
| NOL3 | −0.1044402373747570 |
| MIEN1 | 0.0607555452253983 |
| CENPW | −0.1260999729121140 |
| LY6E | −0.2129142199263660 |
| ALYREF | −0.0867101647370881 |
| MMP1 | −0.0499993277954095 |
| NDUFB10 | 0.2355873243333520 |

In aspects wherein the at least three genes comprise each of the genes in Table 1, the ridge penalized Cox model coefficient for each gene (B) can be the coefficients put forth in Table 1.

In some aspects of the methods of the present disclosure, stratifying the subject based upon the calculated risk score can comprise stratifying the subject as having a low risk for breast cancer recurrence if the risk score is less than a predetermined cutoff value. In some aspects, the predetermined cutoff value can be 49. Thus, in some aspects of the methods of the present disclosure, stratifying the subject based upon the calculated risk score can comprise stratifying the subject as having a low risk for breast cancer recurrence if the risk score is less than 49.

In some aspects of the methods of the present disclosure, stratifying the subject based upon the calculated risk score can comprise stratifying the subject as having a high risk for breast cancer recurrence if the risk score is greater than a predetermined cutoff value. In some aspects, the predetermined cutoff value can be 59. Thus, in some aspects of the methods of the present disclosure, stratifying the subject based upon the calculated risk score can comprise stratifying the subject as having a high risk for breast cancer recurrence if the risk score is greater than 59.

In some aspects of the methods of the present disclosure, stratifying the subject based upon the calculated risk score can comprise stratifying the subject has having an intermediate risk for breast cancer recurrence if the risk score is greater than or equal to a first predetermined cutoff value and less than or equal to a second predetermined cutoff value. In some aspects the first predetermined cutoff value can be 49 and the second predetermined cutoff value can be 59. Thus, in some aspects of the methods of the present disclosure, stratifying the subject based upon the calculated risk score can comprise stratifying the subject as having an intermediate risk for breast cancer recurrence if the risk score is greater than or equal to 49 and less than or equal to 59.

In some aspects, a method of the present disclosure can have a clinical treatment score (CTS) for 10-year risk of distant metastasis of at least about 141.

In some aspects, determining the expression level of a gene in a sample from a subject can comprise determining the quantification cycle (Cq) for the gene using quantitative PCR. In some aspects, the risk score can be calculated according to the following formula:

$$\text{Risk Score} = \frac{(0.03604)\times\left(\sum_i \beta_i \times Cq_{normalized}\right) + pT + pN}{5.64032}$$

wherein

- i is the summation index for the genes for which the expression level was measured;
- β is the ridge penalized Cox model coefficient for each gene as put forth in any one of Tables 1-4; and
- $Cq_{normalized}$ is the normalized average Cq for each of the genes for which the expression level was measured;

wherein

- pT is 0.45542 if the tumor size of the at least one breast cancer tumor is determined to be pT1c; or
- pT is 0.96572 if the tumor size of the breast cancer tumor is determined to be any of pT2, pT3 and pT4; and wherein

- pN is 0.46293 if the nodal status of the at least one breast cancer tumor is determined to be pN1; or
- pN is 1.24922 if the nodal status of the s at least one breast cancer tumor is determined to be pN2.

In some aspects, determining the tumor size of a breast cancer tumor can comprise determining whether the at least one tumor is characterized as pT1c, pT2, pT3 or pT4 using standards and techniques that are known in the art (see Zurrida and Veronesi, *Women's Health,* 2011, 7 (1), 41-49).

In a non-limiting example, a pT1c breast cancer tumor can be a tumor with a size more than 1.0 cm, but not more than 2.0 cm in the greatest dimension.

In a non-limiting example, a pT2 breast cancer tumor can be a tumor with a size more than 2.0 cm, but not more than 5.0 cm in the greatest dimension.

In a non-limiting example, a pT3 breast cancer tumor can be a tumor with a size more than 5.0 cm in the greatest dimension.

In a non-limiting example, a pT4 breast cancer tumor can be a tumor of any size with direct extension to the chest wall (pT4a), to an edema or ulceration of the skin of the breast or satellite skin nodules confined to the same breast (pT4b), to both the chest wall and an edema or ulceration of the skin of the breast or satellite skin nodules confined to the same breast (pT4c) or to an inflammatory carcinoma (pT4d).

In some aspects, determining the nodal status of a breast cancer tumor can comprise determining whether the at least one tumor is characterized as pN1 or pN2 using standards and techniques that are known in the art (see Zurrida and Veronesi, *Women's Health,* 2011, 7 (1), 41-49).

In a non-limiting example, a pN1 breast cancer tumor can be a tumor that has a metastasis in 1 to 3 axillary lymph nodes and/or in internal mammary nodes with microscopic disease detected by sentinel lymph node dissection.

In a non-limiting example, a pN2 breast cancer tumor can be a tumor that has a metastasis in 4-9 axillary lymph nodes or in clinically apparent internal mammary lymph nodes in the absence of axillary lymph node metastasis.

As used herein, the term Cq is used in its broadest sense to refer to the measured quantification cycle (Cq) of a particular gene as measured using quantitative PCR. In some aspects, a Cq can be defined as a limit of detection. In some aspects, a Cq of 35 can be defined as the limit of detection.

Any method of the present disclosure can further comprise determining the 10-year distant recurrence probability for the subject based on the calculated risk score. In some aspects, the 10-year distant recurrence probability ($P_{10}$) can be calculated based on the calculated risk score (R) using the following formula:

$$P_{10} = 1 - \left(0.99514^{e^{(0.05627\times R)}}\right)$$

In some aspects of the methods of the present disclosure, a subject stratified in a high risk group may be administered a treatment that is more aggressive than the treatment administered to a subject stratified in a low risk group. In some aspects of the methods of the present disclosure, a subject stratified in a high risk group may be administered a treatment that is more aggressive than the treatment administered to a subject stratified in an intermediate risk group. In some aspects of the methods of the present disclosure, a subject stratified in an intermediate risk group may be administered a treatment that is more aggressive than the treatment administered to a subject stratified in a low risk group.

In some aspects of the methods of the present disclosure, a subject who has a risk score of greater than 59 may be administered a treatment that is more aggressive than the treatment administered to a subject who has a risk score of less than 49. In some aspects of the methods of the present disclosure, a subject who has a risk score of greater than 59 may be administered a treatment that is more aggressive than the treatment administered to a subject who has a risk score greater than or equal to 49 but less than or equal to 59. In some aspects, a subject who has a risk score greater than 59 may be administered a treatment that is more aggressive than the treatment administered to a subject who has a risk score of less than or equal to 59. In some aspects, a subject who has a risk score greater than or equal 49 may be administered a treatment that is more aggressive than the treatment administered to a subject who has a risk score of less than 49. In some aspects, a subject who has a risk score greater than or equal to 49 and less than or equal to 59 may be administered a treatment that is more aggressive than the treatment administered to a subject who has a risk score of less than 49.

Stratification of subjects into risk groups may be influenced by other features of the subject. For example, risk models can also be derived. As examples, categorizations may be more appropriate for subsets of patients (e.g., pre-post-menopausal or NO N+, treatments).

In some aspects of the methods of the present disclosure, $Cq_{normalized}$ is normalized to the expression of at least one reference gene; in some aspects the at least one referenced gene is a housekeeping gene, e.g., as recited herein. In some aspects, $Cq_{normalized}$ is normalized to the expression of at least one reference gene (e.g., all four genes) selected from the group consisting of GAPDH, GUSB, HPRT1, and TBP. $Cq_{normalized}$ may be calculated according to the following formula: $Cq_{normalized}$=AVG Cq-SF, in which wherein SF is the difference between the AVG Cq value of the reference genes for each subject and a constant reference value K, wherein K=25.012586069, which represents the mean of the AVG Cq of the four reference genes calculated across a plurality of training samples.

Other risk models and formulae may be derived from the disclosure recited herein.

In some aspects of the methods of the present disclosure, a sample can be a biological sample comprising a cancer cell or cancerous tissue. In some aspects of the methods of the present disclosure, a sample can be a breast tissue sample comprising a cancerous cell and/or a cancer stem cell or a primary breast tumor tissue sample. A biological sample can be any sampling of cells, tissues, or bodily fluids in which expression of a breast cancer, stem cell, or stem cell-like gene can be detected. Examples of such biological samples include, but are not limited to, biopsies and smears. Bodily fluids may be useful in the present disclosure and include blood, lymph, urine, saliva, nipple aspirates, gynecological fluids, or any other bodily secretion or derivative thereof when the bodily fluid comprises a cancerous cell and/or a cancer stem cell. Blood can include whole blood, plasma, serum, or any derivative of blood. In some aspects, the biological sample includes breast cancer cells, particularly breast tissue from a biopsy, such as a breast tumor tissue sample, and any derivate thereof, such as three-dimensional structures generated in organotypic cultures in matrices or in suspension cultures (commonly regarded as to mammospheres). Biological samples may be obtained from a subject by a variety of techniques including, for example, by scraping or swabbing an area, by using a needle to aspirate cells or bodily fluids, or by removing a tissue sample (i.e., biopsy). Methods for collecting various biological samples are well known in the art. In some aspects, a breast tissue sample is obtained by, for example, fine needle aspiration biopsy, core needle biopsy, or excisional biopsy. Fixative and staining solutions may be applied to the cells or tissues for preserving the specimen and for facilitating examination. Biological samples, particularly breast tissue samples, may be transferred to a glass slide for viewing under magnification. In some aspects of the methods of the present disclosure, a biological sample can be a formalin-fixed, paraffin-embedded breast tissue sample, particularly a primary breast tumor sample or a cancerous cell. In some aspects of the methods of the present disclosure, a tissue sample can be obtained from a pathologist-guided tissue core sample. In some aspects of the methods of the present disclosure a tissue sample can be a "fresh", i.e., unfixed and/or unfrozen tissue samples (e.g., obtained from a biopsy). In some aspects of the methods of the present disclosure, a tissue sample can be a frozen, unfixed tissue sample.

In some aspects, a sample may be obtained from the subject. A sample may be a tumor obtained from the subject, a cancerous cell obtained from the subject, or a cancer stem cell obtained from the subject. A sample may be a primary cell line derived from a tumor obtained from the subject, from a cancerous cell obtained from the subject, or from a cancer stem cell obtained from the subject.

Breast cancer includes all forms of cancer of the breast. Breast cancer can include primary epithelial breast cancers and any derivate thereof, such as three-dimensional structures generated in organotypic cultures in matrices or in suspension cultures (commonly regarded as to mammospheres). Breast cancer can include cancers in which the mammary tissue breast is involved. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types). A breast cancer that is relevant to the present invention may include familial and hereditary breast cancer.

In some aspects, the breast cancer is ER+/HER2− breast cancer.

A breast cancer relevant to the present invention (e.g., that is treated) can include a localized tumor of the breast. A breast cancer can include a tumor of the breast that is associated with a negative sentinel lymph node (SLN) biopsy. A breast cancer can include a tumor of the breast that is associated with a positive sentinel lymph node (SLN) biopsy. A breast cancer can include a tumor of the breast that is associated with one or more positive axillary lymph nodes, where the axillary lymph nodes have been staged by any applicable method. A breast cancer can include a tumor of the breast that has been typed as having nodal negative status (e.g., node-negative) or nodal positive status (e.g., node-positive). A breast cancer can include a tumor of the breast that has been characterized by receptor status. For example, the receptor status can be hormone receptor negative (e.g., estrogen receptor-positive or estrogen receptor-negative). A breast cancer can include a tumor of the breast that has metastasized to other locations in the body. A breast cancer can be classified as having metastasized to a location selected from the group consisting of bone, lung, liver, lymph nodes, and brain. A breast cancer can be classified according to a characteristic selected from the group consisting of metastatic, localized, regional, local-regional, locally advanced, distant, multicentric, bilateral, ipsilateral, contralateral, newly diagnosed, recurrent, and inoperable.

As used herein, a "subject in need thereof" is a subject having breast cancer or presenting with one or more symptoms of breast cancer, a subject suspected of having breast cancer, a subject having undiagnosed breast cancer, or a subject actually diagnosed with breast cancer. In some aspects, a subject in need thereof has a diagnosed breast cancer. The breast cancer can be primary breast cancer, locally advanced breast cancer or metastatic breast cancer. A "subject" includes a mammal. The mammal can be any mammal, e.g., a human, a primate, a mouse, a rat, a dog, a cat, a cow, a horse, a goat, a camel, a sheep and a pig. In some aspects, the subject is human. The subject may be a male or a female. The subject may have been diagnosed by a skilled artisan as having a breast cancer and is included in a subpopulation of humans who currently have breast cancer or had breast cancer. The subject that has breast cancer may be pre-mastectomy or post-mastectomy.

In some aspects, the methods of the present invention can further comprise determining at least one of, a combination of, or each of, the following: tumor grade, intrinsic subtype, histological type, perivascular infiltration, Ki-67 status, estrogen receptor (ER) status, progesterone receptor (PgR) status, and/or HER2/ERBB2 status.

In some aspects of the methods of the present disclosure, determining the expression level of a gene can comprise any method available in the art for detecting gene expression of the breast cancer, stem cell, or stem cell-like genes. By "detecting expression" is intended determining the quantity or presence of an RNA transcript or its expression product of a gene. Non-limiting examples of methods for detecting gene expression include but are not limited to analysis of single strand conformation polymorphism, capillary electrophoresis, denaturing high performance liquid chromatography, digital molecular barcoding technology, e.g., NANOSTRING® nCounter® system, direct sequencing, DNA mismatch-binding protein assays, dynamic allele-specific hybridization, Fluorescent in situ hybridization (FISH), high-density oligonucleotide SNP arrays, high-resolution melting analysis, microarray, next generation sequencing (NGS), e.g., using the ILLUMINA® Genome Analyzer, ABI Solid instrument, ROCHE® 454 instrument, Heliscope instrument, Northern blot analysis, nuclease protection analysis, oligonucleotide ligase assays, polymerase chain reaction (PCR), primer extension assays, QUANTIGENE® analysis, quantitative nuclease-protection assay (qNPA), reporter gene detection, restriction fragment length polymorphism (RFLP) assays, reverse transcription and real-time quantitative polymerase chain reaction (RT-qPCR), reverse transcription-polymerase chain reaction (RT-PCR), RNA sequencing (RNA-seq), Serial analysis of gene expression (SAGE), Single Molecule Real Time (SMRT) DNA sequencing technology, SNPLex, Southern blot analysis, SYBR® Green chemistry, TAQMAN®-based assays, temperature gradient gel electrophoresis (TGGE), Tiling array, Western blot analysis, and immunohistochemistry.

Methods for detecting expression of the genes of the disclosure, that is, gene expression profiling, include methods based on hybridization analysis of polynucleotides, methods based on sequencing of polynucleotides, immunohistochemistry methods, and proteomics-based methods. In some aspects, PCR-based methods, such as reverse transcription PCR (RT-PCR) (Weis et al., TIG 8:263-64, 1992), and array-based methods such as microarray (Schena et al., Science 270:467-70, 1995) can be used. By "microarray" is intended an ordered arrangement of hybridizable array elements, such as, for example, polynucleotide probes, on a substrate. The term "probe" refers to any molecule that is capable of selectively binding to a specifically intended target biomolecule, for example, a nucleotide transcript or a protein encoded by or corresponding to an intrinsic gene. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Many expression detection methods use isolated RNA. The starting material is typically total RNA isolated from a biological sample, such as a tumor or cell line derived from a tumor (i.e., a primary cell line), and corresponding normal tissue or cell line (e.g., which may serve as a control), respectively. If the source of RNA is a primary tumor, RNA (e.g., mRNA) can be extracted, for example, from frozen or archived paraffin-embedded and fixed (e.g., formalin-fixed) tissue samples (e.g., pathologist-guided tissue core samples) and "fresh", i.e., unfixed and/or unfrozen tissue samples (e.g., obtained from a biopsy).

General methods for RNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker, Lab Invest. 56: A67, (1987); and De Andres et al. Biotechniques 18:42-44, (1995). In particular, RNA isolation can be performed using a purification kit, a buffer set and protease from commercial manufacturers, such as QIAGEN® (Valencia, CA), according to the manufacturer's instructions. For example, total RNA from cells in culture can be isolated using QIAGEN® RNeasy® mini-columns. Other commercially available RNA isolation kits include MASTERPURE™ Complete DNA and RNA Purification Kit (EPICENTRE®, Madison, Wis.) and Paraffin Block RNA Isolation Kit (AMBION®, Austin, TX). Total RNA from tissue samples can be isolated, for example, using RNA Stat-60 (Tel-Test, Friendswood, TX). Total RNA from FFPE can be isolated, for example, using High Pure FFPE RNA Microkit, Cat No. 04823125001 (ROCHE® Applied Science, Indianapolis, IN). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155).

In some aspects, a method for determining the level of gene expression in a sample involves the process of nucleic acid amplification, for example, by RT-PCR (U.S. Pat. No. 4,683,202), ligase chain reaction (Barany, PNAS USA 88:189-93, (1991)), self-sustained sequence replication (Guatelli et al., Proc. Natl. Acad. Sci USA 87:1874-78, (1990)), transcriptional amplification system (Kwoh et al., Proc. Natl. Acad. Sci USA 86:1173-77, (1989)), Q-Beta Replicase (Lizardi et al., Bio/Technology 6:1197, (1988)), rolling circle replication (U.S. Pat. No. 5,854,033), or any other nucleic acid amplification method, followed by the detection of the amplified molecules using techniques well known to those of skill in the art. These detection schemes are especially useful for the detection of nucleic acid molecules if such molecules are present in very low numbers.

In some aspects, intrinsic gene expression is assessed by quantitative RT-PCR. Numerous different PCR or QPCR protocols are known in the art and exemplified herein below and can be directly applied or adapted for use using the presently-described compositions for the detection and/or quantification of the genes listed herein. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR. However, preferred are cyclers with real time fluorescence measurement capabilities, for example, SMARTCYCLER® (CEPHEID®. Sunnyvale, CA), ABI PRISM 7700® (Applied Biosystems, Foster City, Calif.), ROTOR-GENE™ (Corbett Research, Sydney, Australia), LIGHTCYCLER® (ROCHER Diagnostics Corp, Indianapolis, Ind.), ICYCLER® (BIO-RAD® Laboratories, Hercules, Calif.) and MX4000® (Stratagene, La Jolla, Calif.).

In some aspects, microarrays are used for expression profiling. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316. High-density oligonucleotide arrays are particularly useful for determining the gene expression for a large number of RNAs in a sample.

In methods of the present invention, gene expression is normalized to the expression of at least one reference gene. The at least one reference gene may be a housekeeping gene. Exemplary housekeeping genes include and are not limited to AAAS, AAGAB, AAMP, AAR2, AARS, AARS2, AARSD1, AASDHPPT, AATF, ABCB10, ABCB7, ABCD3, ABCE1, ABCF1, ABCF2, ABCF3, ABHD10, ABHD12, ABHD13, ABHD14A, ABHD16A, ABHD4, ABHD8, ABI1, ABT1, ACAD9, ACADVL, ACAP3, ACBD3, ACBD5, ACBD6, ACIN1, ACLY, ACOT13, ACOT8, ACOT9, ACOX1, ACOX3, ACP1, ACSF3, ACSL3, ACSS2, ACTR10, ACTR1A, ACTR1B, ACTR5, ACTR8, ACVR1, ACVR1B, ADCK2, ADCK4, ADH5, ADI1, ADIPOR1, ADIPOR2, ADK, ADNP, ADO, ADPRH, ADPRHL2, ADPRM, ADSL, AES, AFF4, AFTPH, AGFG1, AGGF1, AGPAT1, AGPAT3, AGPAT6, AGPS, AHCY, AHSA1, AIMP1, AIP, AK2, AK3, AKAP8, AKAP9, AKIP1, AKIRIN1, AKIRIN2, AKR1A1, AKR7A2, AKT1, AKTIS1, AKTIP, ALAD, ALDH3A2, ALDH9A1, ALG11, ALG5, ALG8, ALG9, ALKBH1, ALKBH2, ALKBH3, ALKBH5, ALS2, ALYREF, AMBRA1, AMD1, ANAPC10, ANAPC11, ANAPC13, ANAPC15, ANAPC16, ANAPC2, ANAPC5, ANAPC7, ANKFY1, ANKH, ANKHD1, ANKHD1-EIF4EBP3, ANKRD10, ANKRD17, ANKRD28, ANKRD39, ANKRD46, ANO6, ANP32A, ANP32B, ANP32C, ANP32E, ANXA6, ANXA7, AP1B1, AP1G1, AP1M1, AP2A1, AP2A2, AP2M1, AP2S1, AP3B1, AP3D1, AP3M1, AP3S1, AP3S2, AP4B1, AP5M1, APEH, APEX1, APEX2, APHIA, API5, APIP, APOA1BP, APOL2, APOOL, APOPT1, APPL2, APTX, ARAF, ARCN1, ARF1, ARF5, ARF6, ARFGAP2, ARFGAP3, ARFGEF2, ARFIP1, ARFIP2, ARFRP1, ARHGAP35, ARHGAP5, ARHGDIA, ARHGEF10L, ARHGEF11, ARHGEF40, ARIH1, ARIH2, ARIH2OS, ARLI, ARL14EP, ARL5A, ARL6IP4, ARL8A, ARL8B, ARMC1, ARMC10, ARMC5, ARMC6, ARMC7, ARMC8, ARMCX3, ARMCX5, ARNT, ARPC1A, ARPC2, ARPC5L, ARV1, ASB1, ASB6, ASB7, ASB8, ASCC1, ASCC3, ASF1A, ASH2L, ASNA1, ASNSD1, ASPSCR1, ASUN, ASXL1, ATAD1, ATAD3A, ATE1, ATF1, ATF2, ATF4, ATF6, ATF7, ATF7IP, ATG12, ATG13, ATG16L1, ATG2A, ATG2B, ATG3, ATG4B, ATG4D, ATG5, ATG7, ATIC, ATL2, ATMIN, ATOX1, ATP2C1, ATP5A1, ATP5B, ATP5C1, ATP5D, ATP5F1, ATP5G2, ATP5G3, ATP5H, ATP5J, ATP5J2, ATP5J2-PTCD1, ATP5L, ATP50, ATP5S, ATP5SL, ATP6AP1, ATP6V0A2, ATP6V0B, ATP6V0C, ATP6V0D1, ATP6V0E1, ATP6V1C1, ATP6VID, ATP6V1E1, ATP6V1F, ATP6V1G1, ATP6V1H, ATPAF2, ATPIF1, ATRA1D, ATRN, ATXN10, ATXN1L, ATXN2, ATXN2L, ATXN7L3, ATXN7L3B, AUH, AUP1, AURKAIP1, AXIN1, AZI2, AZIN1, B3GALT6, B4GALT3, B4GALT5, B4GALT7, BABAM1, BAD, BAG1, BAG4, BAG6, BAHD1, BANF1, BAP1, BAZ1B, BBS4, BCAP29, BCAP31, BCAS2, BCAT2, BCC1P, BCKDHA, BCKDK, BCL2L1, BCL2L13, BCL2L2-PABPN1, BCL7B, BCLAF1, BCS1L, BECN1, BFAR, BIRC2, BIVM-ERCC5, BLMH, BLOC1S1, BLOC1S2, BLOC1S3, BLOC1S4, BLOC1S6, BLZF1, BMI1, BMS1, BNIP1, BNIP2, BOD1, BOLA1, BOLA3, BPGM, BPNT1, BPTF, BRAT1, BRD2, BRD4, BRD7, BRD9, BRE, BRF1, BRF2, BRIX1, BRK1, BRMS1, BRPF1, BRPF3, BSDC1, BSG, BTBD2, BTD, BTF3, BUB3, BZW1, C10orf12, C10orf2, C10orf76, C10orf88, C11orf1, C11orf24, C11orf31, C11orf57, C11orf58, C11orf73, C11orf83, C12orf10, C12orf23, C12orf29, C12orf44, C12orf45, C12orf5, C12orf52, C12orf57, C12orf65, C12orf66, C14orf1, C14orf119, C14orf142, C14orf166, C14orf2, C14orf28, C15orf38-AP3S2, C15orf57, C16orf13, C16orf62, C16orf72, C16orf91, C17orf49, C17orf51, C17orf58, C17orf59, C17orf70, C17orf85, C18orf21, C18orf25, C18orf32, C18orf8, C19orf43, C19orf53, C19orf60, C19orf70, C1GALT1, C1QBP, Clorf109, Clorf122, Clorf123, Clorf174, Clorf43, Clorf50, Clorf52, C20orf111, C20orf24, C21orf2, C21orf33, C21orf59, C22orf28, C22orf29, C22orf32, C2orf47, C2orf49, C2orf69, C2orf74, C2orf76, C3orf17, C3orf37, C3orf38, C3orf58, C4orf27, C4orf3, C4orf52, C5orf15, C5orf24, C6orf1, C6orf106, C6orf120, C6orf136, C6orf226, C6orf47, C6orf57, C6orf62, C6orf89, C7orf25, C7orf26, C7orf49, C7orf50, C7orf55, C7orf55-LUC7L2, C7orf73, C8orf33, C8orf40, C8orf59, C8orf76, C8orf82, C9orf123, C9orf16, C9orf37, C9orf64, C9orf69, C9orf78, C9orf89, CAB39, CALCOCO2, CALM1, CALR, CALU, CAMTA1, CAMTA2, CANT1, CANX, CAPN1, CAPN7, CAPNS1, CAPRIN1, CAPZA2, CAPZB, CARKD, CARS, CARS2, CASC3, CASC4, CASP3, CASP7, CASP9, CBR4, CBX3, CBX5, CC2D1A, CC2D1B, CCAR1, CCBL1, CCDC12, CCDC124, CCDC127, CCDC130, CCDC137, CCDC149, CCDC174, CCDC22, CCDC23, CCDC25, CCDC47, CCDC50, CCDC51, CCDC59, CCDC71, CCDC86, CCDC90A, CCDC92, CCDC94, CCM2, CCNB1IP1, CCNDBP1, CCNG1, CCNH, CCNK, CCNL1, CCNL2, CCNY, CCPG1, CCT3, CCT4, CCT5, CCT6A, CCT7, CCT8, CD164, CD320, CD46, CD63, CD81, CD82, CD99L2, CDCl23, CDCl6, CDC23, CDC27, CDC37, CDC37L1, CDC40, CDC42, CDC5L, CDIP1, CDIPT, CDK12, CDK13, CDK16, CDK2AP1, CDK4, CDK5RAP1, CDK8, CDK9, CDS2, CDV3, CDYL, CEBPG, CEBPZ, CECR5, CELF1, CENPB, CENPT, CEP104, CEP57, CEP63, CERK, CERS2, CGGBP1, CHAMP1, CHCHD1, CHCHD2, CHCHD3, CHCHD4, CHCHD5, CHCHD7, CHD1L, CHD4, CHD8, CHERP, CHID1, CHKB, CHMP1A, CHMP2A, CHMP2B, CHMP4A, CHMP4B, CHMP5, CHMP6, CHP1, CHPT1, CHRAC1, CHST12, CHST7, CHTOP, CHUK, CHURC1, CHURC1-FNTB, CIAO1, CIB1, CIC, CINP, CIR1, CIRHIA, CISD1, CISD2, CISD3, CKAP4, CLCC1, CLCN3, CLCN7, CLINT1, CLK3, CLNSIA, CLOCK, CLP1, CLPP, CLPTM1, CLPTMIL, CLPX, CLTA, CLTB, CLTC, CMAS, CMC1, CMC2, CMC4, CMPK1, CNBP, CNIH, CNIH4, CNNM2, CNNM3, CNOT1, CNOT11, CNOT2, CNOT3, CNOT4, CNOT7, CNST, COA1, COA3, COA4, COA5, COA6, COASY, COG1, COG2, COG3, COG4, COG7, COG8, COMMD1, COMMD10, COMMD3, COMMD3-BMI1, COMMD5, COMMD6, COMMD7, COMMD9, COMT, COPA, COPB1, COPB2, COPE, COPG1, COPS2, COPS3, COPS4, COPS5, COPS6, COPS7A, COPS7B, COPS8, COPZ1, COQ10B, COQ2, COQ4, COQ5, COQ6, CORO1C, COX11, COX14, COX15, COX16, COX19, COX20, COX411, COX5B, COX6B1, COX6C, COX7A2, COX7A2L, COX7C, COX8A, CPD, CPNE1, CPNE2, CPNE3, CPOX, CPSF2, CPSF3L, CPSF4, CPSF6, CPSF7, CRADD, CRBN, CRCP, CREB3, CREBZF, CREG1, CRELD1, CRIPAK, CRIPT, CRK, CRKL, CRLS1, CRNKL1, CRTC2, CRY2, CSGALNACT2, CSNK1A1, CSNK1A1L, CSNKID, CSNK1G3, CSNK2A3, CSNK2B, CSRP2BP, CST3, CSTB, CSTF1, CSTF2T, CTAGE5, CTBP1, CTCF, CTDSP2, CTNNA1, CTNNB1, CTNNBIP1, CTNNBL1, CTNND1, CTSA, CTSD, CTTN, CTU2, CUEDC2, CUL1, CUL2, CUL4A, CUL4B, CUL5, CUTA, CUX1, CWC15, CWC22, CWC25, CXXC1, CXXC5, CXorf40A, CXorf40B, CXorf56, CYB5B, CYB5D2, CYB5R3, CYC1, CYFIP1, CYHR1, CYP2U1, D2HGDH, DAD1, DAG1, DAGLB, DALRD3, DAP3, DARS, DARS2, DAXX, DAZAP1, DBT, DCAF10, DCAF11, DCAF12, DCAF13, DCAF5, DCAF7, DCAF8, DCAKD, DCTD, DCTN2, DCTN3, DCTN4, DCTN5, DCTN6, DCTPP1, DCUN1D3, DCUN1D4, DCUNID5, DDA1, DDB1, DDB2, DDOST, DDRGK1, DDX1, DDX10, DDX17, DDX18, DDX19A, DDX19B, DDX21, DDX23, DDX24, DDX27, DDX39B, DDX3X, DDX41, DDX42, DDX46, DDX47, DDX49, DDX54, DDX56, DDX59, DEDD, DEF8, DEGS1, DEK, DENNDIA, DENND4A, DENR, DERA, DERL1, DERL2, DESI1, DEXI, DFFA, DGCR14, DGCR2, DGCR6L, DHPS, DHRS12, DHRS7B, DHX15, DHX16, DHX29, DHX30, DHX32, DHX33, DHX36, DHX38, DHX8, DHX9, DIABLO, DIDO1, DIEXF, DIMT1, DIRC2, DIS3, DIS3L2, DKC1, DLD, DLG1, DLGAP4, DLST, DMAP1, DNAAF2, DNAJA2, DNAJA3, DNAJB11, DNAJB12, DNAJB9, DNAJC10, DNAJC11, DNAJC14, DNAJC17, DNAJC19, DNAJC2, DNAJC21, DNAJC3, DNAJC4, DNAJC5, DNAJC7, DNAJC8, DNAJC9, DNASE2, DNLZ, DNMIL, DNM2, DNTTIP1, DNTTIP2, DOHH, DOLK, DPAGT1, DPH1, DPH2, DPH3, DPH5, DPM1, DPP7, DPY30, DR1, DRAM2, DRAP1, DRG2, DROSHA, DSCR3, DTWD1, DUSP11, DUSP14, DUSP16, DUSP22, DUT, DVL3, DYM, DYNCILI1, DYNLL2, DYNLRB1, DYNLT1, E2F4, E4F1, EAF1, EAPP, EARS2, EBAG9, EBNA1BP2, ECD, ECH1, ECHDC1, ECHS1, ECI1, ECI2, ECSIT, EDC3, EDC4, EDEM3, EDF1, EED, EEF1B2, EEF1E1, EEF2, EEFSEC, EFCAB14, EFHA1, EFR3A, EFTUD1, EFTUD2, EGLN2, EHMT1, EI24, EID2, EIF1, EIFIAD, EIFIB, EIF2A, EIF2AK1, EIF2AK3, EIF2AK4, EIF2B2, EIF2B3, EIF2B4, EIF2B5, EIF2D, EIF2S1, EIF2S2, EIF3A, EIF3B, EIF3D, EIF3E, EIF3G, EIF3H, EIF3I, EIF3J, EIF3K, EIF3L, EIF3M, EIF4A1, EIF4A3, EIF4E2, EIF4G1, EIF4G2, EIF4G3, EIF4H, EIF5, EIF5A, EIF5AL1, EIF5B, EIF6, ELAC2, ELAVL1, ELF2, ELK1, ELK4, ELL2, ELMOD3, ELOVL1, ELP2, ELP3, ELP4, ELP6, EMC1, EMC10, EMC2, EMC3, EMC4, EMC6, EMC7, EMC8, EMC9, EMD, EMG1, ENDOG, ENOPH1, ENSA, ENTPD4, ENTPD6, ENY2, EPC1, EPM2AIP1, EPN1, EPRS, ERAL1, ERAP1, ERCC1, ERCC2, ERCC3, ERCC5, ERGIC2, ERGIC3, ERH, ERI3, ERICH1, ERLEC1, ERO1L, ERP44, ESD, ESF1, ETF1, ETFA, ETFB, ETV6, EWSR1, EXD2, EXOC1, EXOC2, EXOC3, EXOC4, EXOC7, EXOC8, EXOSC1, EXOSC10, EXOSC2, EXOSC4, EXOSC7, EXOSC8, EXT2, EXTL3, FADD, FAF1, FAF2, FAHD1, FAM104B, FAM108A1, FAM108B1, FAM114A2, FAM118B, FAM120A, FAM120AOS, FAM120B, FAM122A, FAM127B, FAM134A, FAM134C, FAM136A, FAM149B1, FAM160A2, FAM160B1, FAM160B2, FAM162A, FAM168B, FAM173A, FAM173B, FAM174A, FAM175B, FAM177A1, FAM178A, FAM192A, FAM199X, FAM200A, FAM204A, FAM206A, FAM208B, FAM20B, FAM210B, FAM32A, FAM35A, FAM3A, FAM50A, FAM50B, FAM58A, FAM63A, FAM73B, FAM8A1, FAM96A, FAM96B, FAM98A, FARS2, FARSA, FARSB, FASTK, FASTKD2, FASTKD5, FBRSL1, FBXL15, FBXL17, FBXL3, FBXL4, FBXL5, FBXL6, FBXO11, FBXO18, FBXO22, FBXO28, FBXO3, FBXO38, FBXO42, FBXO45, FBX06, FBXO7, FBXW11, FBXW2, FBXW4, FBXW5, FBXW7, FCF1, FDFT1, FDPS, FDX1, FECH, FEM1C, FEN1, FEZ2, FGFR1OP2, FH, FIBP, FICD, FIP1L1, FIS1, FIZ1, FKBP3, FKBP8, FKBPL, FKRP, FLAD1, FLCN, FLOT1, FLOT2, FNDC3A, FNTA, FNTB, FOPNL, FOXK2, FOXP4, FOXRED1, FPGS, FPGT, FRA10AC1, FTO, FTSJ1, FTSJ2, FTSJ3, FTSJD1, FTSJD2, FUBP1, FUK, FUNDC2, FXN, FYTTD1, FZR1, G3BP1, GAA, GABARAP, GABARAPL2, GABPB1, GAPDH, GADD45GIP1, GALK2, GALNS, GALNT1, GALNT2, GALT, GANAB, GAPVD1, GARS, GART, GATAD2A, GATAD2B, GATC, GBA, GBA2, GBF1, GCC1, GCDH, GCLC, GCLM, GDE1, GDI2, GDPGP1, GEMIN7, GEMIN8, GET4, GFER, GFM1, GFOD2, GGCT, GGNBP2, GGT7, GHDC, GHI™, GID8, GINM1, GIPC1, GLCE, GLE1, GLG1, GLI4, GLO1, GLRX2, GLRX3, GLRX5, GLT8D1, GLTP, GLTPD1, GLYR1, GMPPA, GMPR2, GNB1, GNB2, GNE, GNL2, GNL3, GNPAT, GNPDA1, GNPNAT1, GNPTG, GNS, GOLGA1, GOLGA2, GOLGA3, GOLGA5, GOLGA7, GOLGB1, GOLPH3, GOLT1B, GOPC, GORASP1, GORASP2, GOSR1, GOSR2, GPAA1, GPANK1, GPATCH4, GPBP1, GPBP1L1, GPHN, GPI, GPKOW, GPN1, GPN2, GPN3, GPR107, GPR108, GPS1, GPS2, GPX4, GRAMD4, GRHPR, GRINA, GRIPAP1, GRPEL1, GRSF1, GRWD1, GSK3A, GSK3B, GSPT1, GSPT2, GSR, GSS, GSTK1, GSTM4, GSTO1, GTDC2, GTF2A1, GTF2B, GTF2F1, GTF2F2, GTF2H1, GTF2H4, GTF2H5, GTF2I, GTF3A, GTF3C1, GTF3C2, GTF3C3, GTF3C5, GTF3C6, GTPBP10, GTPBP4, GTPBP5, GTPBP8, GUK1, GUSB, GZF1, H1FX, H2AFV, H2AFX, H2AFY, H2AFZ, HADH, HADHA, HAGH, HARS, HARS2, HAT1, HAUS3, HAUS4, HAUS7, HAX1, HBP1, HBSIL, HCCS, HCFC1, HDAC2, HDAC3, HDAC6, HDAC8, HDDC3, HDGF, HDHD3, HDLBP, HEATR2, HEATR5A, HEBP1, HECTD3, HELZ, HEMK1, HERC4, HERPUD1, HERPUD2, HEXA, HEXDC, HEXIM1, HGS, HIAT1, HIATL1, HIBADH, HIGDIA, HIGD2A, HINFP, HINT1, HINT2, HIST1H2BC, HIVEP1, HMBS, HMG20A, HMG20B, HMGB1, HMGN3, HMGXB3, HMGXB4, HMOX2, HN1L, HNRNPAO, HNRNPA2B1, HNRNPAB, HNRNPC, HNRNPD, HNRNPF, HNRNPH1, HNRNPH2, HNRNPK, HNRNPL, HNRNPM, HNRNPR, HNRNPU, HNRNPUL1, HNRNPUL2, HNRPDL, HNRPLL, HPRT1, HP1BP3, HPS1, HPS6, HS1BP3, HS2ST1, HS6ST1, HSBP1, HSCB, HSD17B10, HSD17B12, HSD17B4, HSPA14, HSPA4, HSPA5, HSPA8, HSPA9, HSPBP1, HSPE1-MOB4, HTATIP2, HTRA2, HTT, HUS1, HUWE1, HYOU1, HYPK, IAH1, IARS, IARS2, IBA57, IBTK, ICK, ICMT, ICT1, IDE, IDH3A, IDH3B, IDH3G, IDI1, IER3IP1, IFNAR1, IFNGR1, IFRD1, IFT27, IKZF5, IL13RA1, IL6ST, ILF2, ILKAP, ILVBL, IMMT, IMP3, IMP4, IMPAD1, INF2, ING1, INO80B, INO80E, INPP5A, INPP5K, INSIG2, INTS1, INTS10, INTS12, INTS3, INTS4, INVS, IP6K1, IP6K2, IPO7, IPO8, IPO9, IRAK1, IREB2, IRF2BP1, IRF2BP2, IRF2BPL, IRGQ, ISCU, ISOC2, IST1, ISY1, ISY1-RAB43, ITCH, ITFG1, ITFG3, ITGB1, ITGB1BP1, ITM2B, ITPA, ITPK1, ITPKC, ITPRIPL2, IVNS1ABP, IWS1, JAGN1, JAK1, JKAMP, JMJD4, JMJD6, JMJD7, JMJD8, JOSD2, JTB, JUND, KANSL2, KANSL3, KARS, KAT2B, KAT5, KAT8, KBTBD2, KBTBD4, KBTBD7, KCMF1, KCTD20, KCTD21, KCTD6, KDM2A, KDM4A, KDM5C, KDSR, KHDRBS1, KHNYN, KHSRP, KIAA0100, KIAA0141, KIAA0195, KIAA0196, KIAA0232, KIAA0319L, KIAA0391, KIAA0754, KIAA0947, KIAA1143, KIAA1191, KIAA1429, KIAA1430, KIAA1586, KIAA1704, KIAA1715, KIAA1919, KIAA1967, KIAA2013, KLC4, KLF3, KLF9, KLHDC2, KLHDC3, KLHL20, KLHL25, KLHL36, KLHL5, KLHL8, KPNA1, KPNB1, KRCC1, KRR1, KTI12, KTN1, KXD1, L3MBTL2, LACTB, LAGE3, LAMP1, LAMP2, LAMTOR1, LAMTOR2, LAMTOR3, LAMTOR4, LAMTOR5, LAP3, LAPTM4A, LARP1, LARP4, LARP7, LARS2, LCOR, LDHA, LEMD2, LENG1, LEPROT, LETM1, LETMD1, LGALSL, LHPP, LIAS, LIG3, LIG4, LIN37, LIN54, LIN7C, LINS, LIPT1, LMAN1, LMBRD1, LMF2, LMO4, LNX2, LOC100129361, LOC100289561, LOC441155, LOC729020, LONP1, LONP2, LPCAT3, LPIN1, LPPR2, LRFN3, LRPAP1, LRPPRC, LRRC14, LRRC24, LRRC28, LRRC40, LRRC41, LRRC42, LRRC47, LRRC57, LRRC59, LRRC8A, LRRFIP2, LRSAM1, LSG1, LSM1, LSM10, LSM14A, LSM14B, LSM2, LSM3, LSM4, LSM5, LSM6, LSM7, LSMD1, LSS, LTV1, LUC7L2, LUC7L3, LUZP6, LYRM1, LYRM4, LYRM5, LYSMD1, LYSMD3, LYSMD4, LZTR1, M6PR, MAD2L1BP, MAD2L2, MAEA, MAGED1, MAGEF1, MAGOH, MAGT1, MAK16, MALSU1, MANIA2, MAN1B1, MAN2A2, MAN2B2, MAN2C1, MAPILC3B2, MAP2K1, MAP2K2, MAP2K5, MAP3K7, MAP4K4, MAPK1, MAPK1IPIL, MAPK6, MAPK8, MAPK9, MAPKAP1, MAPKAPK2, MAPKAPK5, MAPRE2, MARCH2, MARCH5, MARCH6, MARCH7, MARK3, MARK4, MARS, MARS2, MAT2B, MAVS, MAX, MAZ, MBD1, MBD2, MBD3, MBD4, MBLAC1, MBNL2, MBTPS1, MBTPS2, MCAT, MCCC1, MCEE, MCFD2, MCM3AP, MCM7, MCMBP, MCOLN1, MCPH1, MCRS1, MCTS1, MCU, MDC1, MDP1, ME2, MEAF6, MECP2, MED10, MED11, MED13, MED14, MED16, MED19, MED20, MED21, MED24, MED29, MED31, MED4, MED6, MED7, MED8, MEF2A, MEF2BNB, MEMO1, MEN1, MEPCE, METAP1, METAP2, METRN, METTL13, METTL14, METTL16, METTL17, METTL18, METTL20, METTL21A, METTL23, METTL2A, METTL2B, METTL3, METTL5, MFAP1, MFAP3, MFF, MFN1, MFSD11, MFSD12, MFSD3, MFSD5, MGAT2, MGAT4B, MGME1, MGMT, MGRN1, MGST3, MIA3, MIB1, MICALL1, MICU1, MID1IP1, MIDN, MIEN1, MIER1, MIF, MIF4GD, MIIP, MINOS1, MIS12, MITD1, MKI67IP, MKKS, MKLN1, MKNK1, MKRN2, MLEC, MLF2, MLH1, MLLT1, MLLT10, MLST8, MLX, MMAA, MMADHC, MMS19, MNAT1, MNF1, MOB4, MOGS, MONIA, MON2, MORC2, MORF4L2, MOSPD1, MPC2, MPDU1, MPG, MPHOSPH10, MPI, MPLKIP, MPND, MPPE1, MPV17L2, MRFAP1, MRFAP1L1, MRI1, MRM1, MRP63, MRPL1, MRPL10, MRPL11, MRPL12, MRPL13, MRPL14, MRPL15, MRPL16, MRPL17, MRPL18, MRPL19, MRPL2, MRPL20, MRPL21, MRPL22, MRPL23, MRPL24, MRPL27, MRPL28, MRPL3, MRPL30, MRPL32, MRPL33, MRPL35, MRPL36, MRPL37, MRPL38, MRPL4, MRPL40, MRPL41, MRPL42, MRPL43, MRPL44, MRPL45, MRPL46, MRPL47, MRPL48, MRPL49, MRPL50, MRPL51, MRPL52, MRPL53, MRPL54, MRPL55, MRPL9, MRPS10, MRPS11, MRPS12, MRPS14, MRPS15, MRPS16, MRPS17, MRPS18A, MRPS18B, MRPS18C, MRPS2, MRPS21, MRPS22, MRPS23, MRPS24, MRPS25, MRPS26, MRPS27, MRPS28, MRPS30, MRPS31, MRPS33, MRPS34, MRPS35, MRPS5, MRPS6, MRPS7, MRPS9, MRRF, MRS2, MRTO4, MSANTD3, MSH3, MSH6, MSL3, MSMP, MSRA, MSRB2, MTA2, MTCH1, MTCH2, MTDH, MTERFD1, MTERFD2, MTERFD3, MTFMT, MTFR1, MTFR1L, MTIF3, MTM1, MTMR1, MTMR3, MTMR6, MTO1, MTPAP, MTRR, MTSS1, MTX2, MUL1, MUS81, MUT, MVD, MXD4, MXI1, MYBBPIA, MYEOV2, MYL12B, MYNN, MYO1E, MYPOP, MZF1, MZT2A, MZT2B, N4BP1, N4BP2L2, NAA10, NAA15, NAA20, NAA38, NAA50, NAA60, NABP2, NACA, NACA2, NACC1, NACC2, NAE1, NAMPT, NANS, NAPIL4, NAPA, NARF, NARFL, NARG2, NARS, NARS2, NAT10, NBN, NBR1, NCAPH2, NCBP2, NCK1, NCKIPSD, NCL, NCLN, NCOA1, NCOA6, NCOR1, NCSTN, NDEL1, NDFIP1, NDNL2, NDST1, NDUFA10, NDUFA11, NDUFA12, NDUFA13, NDUFA2, NDUFA3, NDUFA4, NDUFA5, NDUFA6, NDUFA7, NDUFA8, NDUFA9, NDUFAF2, NDUFAF3, NDUFAF4, NDUFB10, NDUFB11, NDUFB2, NDUFB3, NDUFB4, NDUFB5, NDUFB6, NDUFB7, NDUFB8, NDUFB9, NDUFC1, NDUFC2, NDUFC2-KCTD14, NDUFS2, NDUFS3, NDUFS4, NDUFS5, NDUFS6, NDUFS7, NDUFS8, NDUFV1, NDUFV2, NECAP1, NEDD8, NEDD8-MDP1, NEIL2, NEK4, NEK9, NELFB, NELFCD, NELFE, NENF, NEU1, NF2, NFATC2IP, NFE2L2, NFIL3, NFKBIB, NFKBIL1, NFU1, NFX1, NFYB, NFYC, NGDN, NGLY1, NGRN, NHP2, NHP2L1, NIF3L1, NINJ1, NIP7, NIPA2, NIPBL, NISCH, NIT1, NIT2, NKAP, NKIRAS2, NMD3, NME1-NME2, NME2, NME3, NME6, NMRK1, NMT1, NOA1, NOB1, NOC2L, NOL10, NOL11, NOL12, NOL6, NOL7, NOL8, NOLC1, NOM1, NONO, NOP10, NOP14, NOP16, NOP2, NOP56, NOP58, NOP9, NPC1, NPC2, NPLOC4, NPRL2, NPRL3, NQO2, NR1H2, NR2C1, NR2C2AP, NR3C2, NRBP1, NRDE2, NRIP1, NSA2, NSD1, NSDHL, NSFLIC, NSMCE1, NSMCE2, NSMCE4A, NSRP1, NSUN2, NSUN5, NSUN6, NT5C, NT5C3, NT5DC1, NTAN1, NTMT1, NTPCR, NUB1, NUBP1, NUBP2, NUCB1, NUCKS1, NUDC, NUDCD1, NUDCD2, NUDT14, NUDT15, NUDT2, NUDT21, NUDT22, NUDT3, NUDT9, NUFIP2, NUP107, NUP133, NUP153, NUP54, NUP62, NUP85, NUPL2, NUTF2, NXF1, NXT1, OAT, OAZ1, OAZ2, OBFC1, OCEL1, OCIAD1, ODC1, OGFOD1, OGFOD3, OGFR, OGG1, OGT, OLA1, OPA1, OPA3, ORC4, ORMDL1, ORMDL2, ORMDL3, OS9, OSBP, OSBPL2, OSBPL9, OSGEP, OSGIN2, OSTM1, OTUB1, OTUD5, OVCA2, OXAIL, OXNAD1, P4HTM, PA2G4, PABPN1, PACSIN2, PAF1, PAFAH1B1, PAGR1, PAICS, PAIP1, PAIP2, PAK1IP1, PAK2, PAM16, PANK2, PANK3, PANK4, PANX1, PAPD4, PAPD7, PAPOLA, PARK7, PARL, PARN, PARP1, PARP3, PARP9, PATLI, PATZ1, PAXBP1, PBDC1, PBX2, PCBP1, PCBP2, PCDHGB5, PCF11, PCGF1, PCGF5, PCID2, PCIF1, PCM1, PCMT1, PCNA, PCNX, PCNXL4, PCSK7, PCYOX1, PCYTIA, PDAP1, PDCD2, PDCD5, PDCD6, PDCD6IP, PDE12, PDE6D, PDGFC, PDHB, PDHX, PDK2, PDLIM5, PDP2, PDS5A, PDZD11, PDZD8, PEBP1, PEF1, PELO, PELP1, PEPD, PES1, PET100, PET117, PEX1, PEX11A, PEX11B, PEX12, PEX13, PEX14, PEX16, PEX19, PEX2, PEX26, PEX5, PEX6, PFDN2, PFDN4, PFDN5, PFDN6, PFN1, PGAM5, PGBD3, PGK1, PGLS, PGP, PGPEP1, PGRMC2, PHACTR4, PHAX, PHB, PHB2, PHC2, PHF10, PHF12, PHF20L1, PHF23, PHF5A, PHKB, PHPT1, PHRF1, PI4K2A, PI4KA, PI4 KB, PIAS1, PICALM, PICK1, PIGC, PIGF, PIGG, PIGH, PIGK, PIGP, PIGS, PIGT, PIGU, PIGW, PIGX, PIGY, PIH1D1, PIK3C3, PIK3CB, PIK3R1, PIK3R4, PIN1, PINK1, PINX1, PIP5K1A, PITHD1, PITPNA, PITPNB, PITRM1, PLA2G12A, PLAA, PLBD2, PLD3, PLEKHA1, PLEKHJ1, PLEKHM1, PLGRKT, PLIN3, PLOD1, PLOD3, PLRG1, PMF1, PMF1-BGLAP, PMPCA, PMPCB, PMS1, PMVK, PNISR, PNKD, PNKP, PNN, PNO1, PNPLA6, PNPLA8, PNPO, PNPT1, PNRC2, POFUT1, POLD2, POLDIP2, POLDIP3, POLE3, POLE4, POLG, POLH, POLK, POLL, POLM, POLRIC, POLRID, POLRIE, POLR2A, POLR2B, POLR2C, POLR2D, POLR2E, POLR2F, POLR2G, POLR2H, POLR2I, POLR2J, POLR2K, POLR2L, POLR3C, POLR3E, POLR3GL, POLR3K, POM121, POM121C, POMGNT1, POMP, POMT1, POP4, POP5, POP7, PPA1, PPA2, PPAN, PPAN-P2RY11, PPARA, PPARD, PPCS, PPFIA1, PPHLN1, PPID, PPIE, PPIF, PPIG, PPIH, PPIL4, PPMIA, PPM1B, PPPICA, PPPICC, PPP1R10, PPP1R11, PPP1R15B, PPP1R37, PPP1R7, PPP1R8, PPP2CA, PPP2CB, PPP2R1A, PPP2R2A, PPP2R2D, PPP2R3C, PPP2R4, PPP2R5A, PPP2R5B, PPP2R5C, PPP2R5D, PPP2R5E, PPP4C, PPP4R1, PPP4R2, PPP5C, PPP6C, PPP6R2, PPP6R3, PPWD1, PQBP1, PQLC1, PQLC2, PRADC1, PRCC, PRDM4, PRDX1, PRDX2, PRDX3, PRDX5, PRDX6, PREB, PREP, PRKAA1, PRKAB1, PRKACA, PRKAG1, PRKARIA, PRKRIP1, PRMT1, PRMT5, PRMT7, PROSC, PRPF18, PRPF19, PRPF3, PRPF31, PRPF4, PRPF40A, PRPF4B, PRPF6, PRPF8, PRPS1, PRPSAP1, PRR14, PRRC1, PRRC2A, PRRC2B, PRUNE, PSEN1, PSEN2, PSENEN, PSKH1, PSMA1, PSMA2, PSMA3, PSMA4, PSMA5, PSMA6, PSMA7, PSMB1, PSMB2, PSMB3, PSMB4, PSMB5, PSMB6, PSMB7, PSMC2, PSMC3, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME3, PSMF1, PSMG2, PSMG3, PSMG4, PSPC1, PTCD1, PTCD3, PTDSS1, PTEN, PTGES2, PTGES3, PTOV1, PTP4A2, PTPMT1, PTPN1, PTPN11, PTPN23, PTRH1, PTRH2, PTRHD1, PUF60, PUM1, PUM2, PURA, PURB, PUS3, PUS7, PUSL1, PWP1, PWP2, PWWP2A, PXMP4, PYCR2, PYGO2, PYURF, QARS, QRICH1, QRSL1, QSOX1, QTRT1, R3HCC1, R3HDM2, RAB10, RAB11A, RAB11B, RAB14, RAB18, RABIA, RAB1B, RAB21, RAB22A, RAB2A, RAB2B, RAB3GAP1, RAB3GAP2, RAB40C, RAB4A, RAB5A, RAB5B, RAB5C, RAB6A, RAB7A, RAB9A, RABEP1, RABEPK, RABGEF1, RABGGTA, RABGGTB, RAD1, RAD17, RAD23B, RAD50, RAD51C, RAF1, RALA, RALBP1, RALY, RAN, RANBP1, RANBP2, RANBP3, RANBP6, RANGAP1, RANGRF, RAPIA, RAPGEF1, RAPGEF2, RARS, RARS2, RB1CC1, RBAK, RBBP4, RBBP7, RBCK1, RBFA, RBM10, RBM12, RBM12B, RBM14, RBM14-RBM4, RBM15, RBM15B, RBM17, RBM18, RBM19, RBM23, RBM27, RBM28, RBM33, RBM34, RBM39, RBM4, RBM41, RBM42, RBM5, RBM6, RBM7, RBM8A, RBMX, RBMXL1, RBX1, RC3H2, RCAN1, RCHY1, RCN2, RDH14, RDX, REEP3, REEP5, RELA, REPIN1, REPS1, RER1, REST, REXO1, RFC1, RFC2, RFC5, RFK, RFNG, RFT1, RFWD2, RFXANK, RGP1, RHBDD1, RHBDD3, RHOA, RHOB, RHOT1, RHOT2, RIC8A, RIN2, RING1, RINT1, RIOK1, RIOK2, RIOK3, RIPK1, RMDN1, RMDN3, RMI1, RMND1, RMND5A, RMND5B, RNASEH1, RNASEH2C, RNASEK, RNF10, RNF103, RNF11, RNF111, RNF113A, RNF115, RNF121, RNF126, RNF13, RNF14, RNF141, RNF146, RNF167, RNF181, RNF185, RNF187, RNF216, RNF220, RNF25, RNF26, RNF31, RNF34, RNF4, RNF40, RNF5, RNF6, RNF7, RNH1, RNMTL1, RNPEP, ROMO1, RP9, RPA2, RPA3, RPAIN, RPAP3, RPF1, RPF2, RPL10A, RPL11, RPL14, RPL26L1, RPL27, RPL30, RPL31, RPL32, RPL34, RPL35, RPL35A, RPL36AL, RPL4, RPL6, RPL7L1, RPL8, RPN1, RPN2, RPP14, RPP25L, RPP30, RPP38, RPRD1B, RPS13, RPS19BP1, RPS23, RPS24, RPS27L, RPS5, RPS6, RPS6KA3, RPS6KB1, RPS6KB2, RPUSD3, RQCD1, RRAGA, RRM1, RRN3, RRNAD1, RRP1, RRP36, RRP7A, RRP8, RRS1, RSAD1, RSBNIL, RSC1A1, RSLID1, RSPRY1, RSRC1, RSRC2, RTCA, RTFDC1, RTN4, RUFY1, RUVBL1, RWDD1, RWDD3, RXRA, RXRB, SAE1, SAMD1, SAMD4B, SAMD8, SAMM50, SAP18, SAP30, SAP30BP, SAP30L, SARIA, SARNP, SARS, SART1, SART3, SAT2, SAV1, SBDS, SCAF1, SCAF11, SCAF4, SCAF8, SCAMP2, SCAMP3, SCAND1, SCAP, SCARB2, SCFD1, SCFD2, SCNM1, SCO1, SCO2, SCOC, SCP2, SCRIB, SCRN3, SCYL1, SCYL2, SCYL3, SDAD1, SDCBP, SDCCAG3, SDCCAG8, SDE2, SDF2, SDF4, SDHA, SDHAF2, SDHB, SDHC, SDHD, SDR39U1, SEC11A, SEC13, SEC16A, SEC22B, SEC22C, SEC23A, SEC23IP, SEC24A, SEC24B, SEC24C, SEC31A, SEC61A1, SEC61B, SEC61G, SEC62, SEC63, SECISBP2, SEHIL, SELIL, SELK, SELO, SELRC1, SELT, SENP2, SENP3, SENP5, SENP6, SEPHS1, SERBP1, SERF2, SERGEF, SERINC1, SERINC3, SERPINB6, SERTAD2, SET, SETD2, SETD3, SETD5, SETD6, SETD7, SETD8, SETDB1, SF1, SF3A1, SF3A3, SF3B1, SF3B14, SF3B2, SF3B3, SF3B4, SF3B5, SFSWAP, SGK196, SGMS1, SGPL1, SGSM3, SGTA, SH3BP5L, SH3GLB1, SHARPIN, SHOC2, SIAH1, SIAH2, SIGMAR1, SIKE1, SIL1, SIRT2, SIRT3, SIRT5, SIRT6, SIVA1, SKIL, SKIV2L, SKIV2L2, SKP1, SLC15A4, SLC20A1, SLC25A11, SLC25A26, SLC25A28, SLC25A3, SLC25A32, SLC25A38, SLC25A39, SLC25A44, SLC25A46, SLC25A5, SLC27A4, SLC30A1, SLC30A5, SLC30A9, SLC35A2, SLC35A4, SLC35B1, SLC35B2, SLC35C2, SLC35E1, SLC35E3, SLC35F5, SLC38A2, SLC39A1, SLC39A3, SLC39A7, SLC41A3, SLC46A3, SLC48A1, SLIRP, SLMO2, SL™, SMAD2, SMAD4, SMAD5, SMAP1, SMARCA2, SMARCA4, SMARCALI, SMARCB1, SMARCE1, SMCIA, SMC5, SMCR7L, SMEK1, SMEK2, SMG5, SMG7, SMG8, SMIM11, SMIM12, SMIM8, SMNDC1, SMPD1, SMPD4, SMU1, SMUG1, SNAP23, SNAP29, SNAP47, SNAPC3, SNAPC5, SNAPIN, SND1, SNF8, SNRNP200, SNRNP25, SNRNP27, SNRNP35, SNRNP40, SNRNP48, SNRNP70, SNRPA, SNRPB, SNRPB2, SNRPC, SNRPD1, SNRPD2, SNRPD3, SNRPG, SNUPN, SNW1, SNX12, SNX13, SNX17, SNX18, SNX19, SNX2, SNX25, SNX3, SNX4, SNX5, SNX6, SNX9, SOCS4, SOCS6, SOD1, SON, SPAG7, SPAG9, SPATA2, SPATA5L1, SPCS1, SPCS3, SPECCIL, SPEN, SPG11, SPG21, SPG7, SPHAR, SPNS1, SPOP, SPPL2B, SPPL3, SPRYD3, SPRYD7, SPSB3, SPTSSA, SPTY2D1, SRA1, SRD5A3, SREBF2, SREK1IP1, SRM, SRP14, SRP19, SRP54, SRP68, SRP72, SRP9, SRPR, SRPRB, SRR, SRRD, SRRM1, SRSF1, SRSF10, SRSF11, SRSF2, SRSF3, SRSF4, SRSF7, SRSF8, SS18L2, SSB, SSBP1, SSNA1, SSR1, SSR2, SSR3, SSRP1, SSSCA1, SSU72, ST3GAL2, ST6GALNAC6, ST7, STAM, STAM2, STAMBP, STARD3, STARD7, STAT3, STAU1, STAU2, STIM1, STIP1, STK11, STK16, STOM, STOML1, STOML2, STRAP, STRIP1, STRN3, STT3A, STT3B, STUB1, STX10, STX17, STX4, STX5, STX8, STXBP3, STYXL1, SUB1, SUCLA2, SUCLG1, SUCLG2, SUGP1, SUGT1, SUMO1, SUMO3, SUN2, SUPT4H1, SUPT5H, SUPT6H, SUPT7L, SUPV3L1, SURF1, SURF4, SURF6, SUV420H1, SUZ12, SYAP1, SYF2, SYMPK, SYNCRIP, SYNJ2BP, SYNJ2BP-COX16, SYPL1, SYS1, SYVN1, SZRD1, TAB1, TAB2, TACO1, TADA1, TADA3, TAF10, TAF11, TAF12, TAF13, TAF15, TAFID, TAF4, TAF5L, TAF8, TAF9, TALDO1, TAMM41, TANGO2, TANGO6, TANK, TAOK2, TAPBP, TAPT1, TARDBP, TARS, TATDN1, TATDN2, TAXIBP1, TAZ, TBC1D1, TBC1D14, TBC1D15, TBC1D20, TBC1D22A, TBC1D23, TBC1D7, TBC1D9B, TBCA, TBCB, TBCC, TBCCD1, TBCD, TBCE, TBK1, TBP, TBRG1, TBRG4, TCAIM, TCEANC2, TCEB1, TCEB2, TCEB3, TCERG1, TCF12, TCF20, TCF25, TCP1, TCTN3, TDP2, TDRD3, TECR, TEF, TEFM, TELO2, TERF2, TERF2IP, TEX2, TEX261, TEX264, TFAM, TFB1M, TFB2M, TFCP2, TFDP1, TFE3, TFG, TFIP11, TFPT, TGIF2-C20orf24, TGOLN2, THADA, THAP3, THAP4, THAP5, THAP7, THOC5, THOC7, THOP1, THRAP3, THTPA, THUMPD3, THYN1, TIA1, TIAL1, TICAM1, TIGD5, TIGD6, TIMM10, TIMM10B, TIMM13, TIMM17A, TIMM17B, TIMM21, TIMM22, TIMM44, TIMM50, TIMM8B, TIMM9, TIMMDC1, TINF2, TIPRL, TJAP1, TLE1, TLK1, TM2D1, TM2D2, TM2D3, TM9SF1, TM9SF2, TM9SF3, TM9SF4, TMBIM1, TMBIM4, TMBIM6, TMCC1, TMCO1, TMCO3, TMED1, TMED10, TMED2, TMED4, TMED5, TMED7, TMED7-TICAM2, TMED9, TMEM101, TMEM106B, TMEM106C, TMEM115, TMEM120A, TMEM126A, TMEM127, TMEM128, TMEM129, TMEM131, TMEM134, TMEM141, TMEM147, TMEM14B, TMEM14C, TMEM161A, TMEM167B, TMEM168, TMEM177, TMEM179B, TMEM18, TMEM184C, TMEM185B, TMEM186, TMEM187, TMEM189, TMEM189-UBE2V1, TMEM19, TMEM192, TMEM199, TMEM203, TMEM205, TMEM214, TMEM219, TMEM222, TMEM223, TMEM230, TMEM242, TMEM248, TMEM251, TMEM256, TMEM258, TMEM259, TMEM30A, TMEM33, TMEM39A, TMEM41A, TMEM41B, TMEM42, TMEM5, TMEM50A, TMEM50B, TMEM55B, TMEM57, TMEM59, TMEM60, TMEM62, TMEM63B, TMEM64, TMEM66, TMEM69, TMEM70, TMEM81, TMEM87A, TMEM9, TMEM9B, TMF1, TMLHE, TMPO, TMUB1, TMUB2, TMX1, TMX2, TMX4, TNFAIP1, TNFAIP8L2-SCNM1, TNIP1, TNKS2, TNPO1, TNPO3, TNRC6A, TOB1, TOLLIP, TOMM20, TOMM22, TOMM40, TOMM5, TOMM6, TOMM7, TOMM70A, TOP1, TOP2B, TOPORS, TORIA, TORIAIP2, TOR1B, TOR3A, TOX4, TP53RK, TPCN1, TPD52L2, TPGS1, TPI1, TPP2, TPRA1, TPRGIL, TPRKB, TPRN, TPST2, TRA2A, TRA2B, TRAF6, TRAF7, TRAP1, TRAPPC1, TRAPPC10, TRAPPC11, TRAPPC12, TRAPPC13, TRAPPC2L, TRAPPC3, TRAPPC4, TRAPPC5, TRAPPC6B, TRAPPC8, TRAPPC9, TRIAP1, TRIM26, TRIM27, TRIM28, TRIM3, TRIM39, TRIM39-RPP21, TRIM41, TRIM44, TRIM56, TRIM65, TRIM8, TRIP12, TRIP4, TRMT1, TRMT10C, TRMT112, TRMT12, TRM-TIL, TRMT2A, TRNAUIAP, TRNT1, TRPC4AP, TRPT1, TRUB2, TSC2, TSEN15, TSEN34, TSFM, TSG101, TSN, TSNAX, TSPAN17, TSPAN31, TSPYL1, TSR1, TSR2, TSR3, TSSC4, TSTA3, TSTD2, TTC1, TTC17, TTC19, TTC32, TTC33, TTC37, TTC4, TTC7B, TTC9C, TTI1, TTI2, TUBA1B, TUBAIC, TUBB, TUBD1, TUBGCP2, TUBGCP4, TUFM, TUSC2, TUT1, TVP23B, TXLNA, TXLNG, TXN2, TXNDC11, TXNDC12, TXNDC15, TXNDC17, TXNDC9, TXNL1, TXNL4A, TXNL4B, TXNRD1, TYK2, TYW1, U2AF1, U2AF1L4, U2AF2, UAP1, UBA1, UBA2, UBA3, UBA5, UBA52, UBAC2, UBALD1, UBAP1, UBAP2L, UBB, UBC, UBE2A, UBE2B, UBE2D2, UBE2D3, UBE2D4, UBE2E1, UBE2E2, UBE2E3, UBE2F, UBE2G2, UBE2H, UBE2I, UBE2J1, UBE2J2, UBE2K, UBE2L3, UBE2M, UBE2N, UBE2NL, UBE2Q1, UBE2R2, UBE2V1, UBE2V2, UBE2W, UBE2Z, UBE3A, UBE3B, UBE3C, UBE4A, UBE4B, UBFD1, UBIAD1, UBL3, UBL4A, UBL5, UBL7, UBOX5, UBP1, UBQLN1, UBQLN2, UBQLN4, UBR2, UBR7, UBTD1, UBTF, UBXN2A, UBXN4, UBXN6, UCHL3, UCHL5, UCK1, UCK2, UCKL1, UEVLD, UFC1, UFD1L, UFL1, UFSP2, UGP2, UHRFIBPIL, ULK1, ULK3, UNC50, UNG, UPF1, UPF2, UPF3B, UPRT, UQCC, UQCR10, UQCR11, UQCRB, UQCRC1, UQCRC2, UQCRHL, UQCRQ, URGCP, URI1, URM1, UROD, UROS, USB1, USE1, USF1, USF2, USP10, USP14, USP16, USP19, USP22, USP25, USP27X, USP33, USP38, USP39, USP4, USP47, USP5, USP7, USP8, USP9X, UTP11L, UTP14A, UTP14C, UTP15, UTP23, UTP3, UTP6, UXS1, UXT, VAC14, VAMP3, VAMP5, VAPA, VAPB, VARS2, VBP1, VCP, VDAC3, VEZT, VIMP, VMA21, VPS16, VPS18, VPS25, VPS26A, VPS26B, VPS28, VPS29, VPS33A, VPS36, VPS37A, VPS4A, VPS51, VPS52, VPS53, VPS72, VRK2, VRK3, VTA1, VTIIA, VTIIB, WAC, WAPAL, WARS2, WBP11, WBP1L, WBP2, WBP4, WBSCR22, WDR1, WDR12, WDR13, WDR18, WDR20, WDR24, WDR25, WDR26, WDR3, WDR33, WDR36, WDR41, WDR43, WDR44, WDR45, WDR45B, WDR46, WDR55, WDR59, WDR5B, WDR6, WDR61, WDR70, WDR73, WDR74, WDR75, WDR77, WDR81, WDR83OS, WDR85, WDR89, WDTC1, WIBG, WIPI2, WIZ, WRAP53, WRB, WRNIP1, WSB2, WTAP, WTH3DI, WWP1, WWP2, XIAP, XPA, XPC, XPNPEP1, XPO1, XPO7, XPOT, XRCC5, XRCC6, XYLT2, YAF2, YARS, YARS2, YIFIA, YIFIB, YIPF1, YIPF3, YIPF4, YIPF5, YIPF6, YKT6, YMEIL1, YPEL2, YRDC, YTHDC1, YTHDF1, YTHDF2, YTHDF3, YWHAB, YWHAE, YY1, YY1AP1, ZADH2, ZBED4, ZBED6, ZBTB1, ZBTB10, ZBTB11, ZBTB14, ZBTB17, ZBTB18, ZBTB21, ZBTB25, ZBTB33, ZBTB39, ZBTB44, ZBTB45, ZBTB5, ZBTB6, ZBTB7A, ZBTB8OS, ZC3H10, ZC3H11A, ZC3H13, ZC3H15, ZC3H18, ZC3H3, ZC3H7A, ZC3H7B, ZCCHC10, ZCCHC11, ZCCHC3, ZCCHC7, ZCCHC9, ZCRB1, ZDHHC14, ZDHHC16, ZDHHC2, ZDHHC3, ZDHHC4, ZDHHC5, ZDHHC8, ZFAND1, ZFAND2B, ZFAND3, ZFAND5, ZFAND6, ZFP91, ZFPL1, ZFR, ZFYVE1, ZFYVE19, ZFYVE27, ZGPAT, ZHX1, ZHX1-$C_8$ORF76, ZHX2, ZHX3, ZKSCAN1, ZMAT2, ZMAT3, ZMAT5, ZMPSTE24, ZMYM2, ZMYND11, ZNF121, ZNF131, ZNF134, ZNF138, ZNF142, ZNF143, ZNF146, ZNF174, ZNF181, ZNF189, ZNF195, ZNF197, ZNF207, ZNF22, ZNF226, ZNF232, ZNF24, ZNF259, ZNF274, ZNF277, ZNF280D, ZNF281, ZNF3, ZNF32, ZNF322, ZNF326, ZNF330, ZNF335, ZNF33A, ZNF343, ZNF347, ZNF37A, ZNF384, ZNF394, ZNF397, ZNF398, ZNF408, ZNF41, ZNF410, ZNF414, ZNF419, ZNF438, ZNF444, ZNF446, ZNF48, ZNF480, ZNF491, ZNF506, ZNF507, ZNF513, ZNF518A, ZNF526, ZNF561, ZNF574, ZNF576, ZNF579, ZNF580, ZNF592, ZNF593, ZNF598, ZNF620, ZNF622, ZNF623, ZNF638, ZNF639, ZNF641, ZNF644, ZNF649, ZNF654, ZNF655, ZNF664, ZNF668, ZNF672, ZNF687, ZNF688, ZNF691, ZNF7, ZNF706, ZNF721, ZNF740, ZNF76, ZNF764, ZNF770, ZNF777, ZNF787, ZNF805, ZNF814, ZNF830, ZNF865, ZNF91, ZNHIT1, ZNHIT3, ZNRD1, ZRANB1, ZRANB2, ZSCAN21, ZSCAN29, ZSCAN32, ZSWIM1, ZSWIM7, ZSWIM8, ZW10, ZXDA, ZXDB, and ZZZ3.

In some aspects, the at least one reference gene can comprise one or more of GAPDH, GUSB, HPRT1, and TBP. More preferably, the at least one reference gene comprises at least each of GAPDH, GUSB, HPRT1, and TBP.

The present disclosure also provides kits useful for determining gene expression of a breast cancer sample and/or providing prognostic information to identify risk of recurrence. These kits can comprise a set of probes and/or primers specific for least two, or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, at least nineteen genes or each of the twenty genes in Table 1. In some aspects, a kit can comprise a set of probes and/or primers specific for EIF4EBP1, MRPS23, and TOP2A. In some aspects, a kit can comprise a set of probes and/or primers specific for APOBEC3B, CENPW, EIF4EBP1, EXOSC4, LY6E, MMP1, MRPS23, NDUFB10, and TOP2A. In some aspects, a kit can comprise a set of probes and/or primers specific for ALYREF, APOBEC3B, CDK1, CENPW, EIF4EBP1, EXOSC4, H2AFJ, LY6E, MIEN1, MMP1, MRPS23, NDUFB10, NOL3, RACGAP1, SFN, and TOP2A.

In some aspects, a kit of the present disclosure can comprise a set of instructions for performing any method of the present disclosure. The instructions can be written instructions. In some aspects the instructions can be on a computer readable medium.

In one embodiment of the present disclosure, the capture probes are immobilized on an array. By "array" is intended a solid support or a substrate with peptide or nucleic acid probes attached to the support or substrate. Arrays typically comprise a plurality of different capture probes that are coupled to a surface of a substrate in different, known locations. The arrays of the disclosure comprise a substrate having a plurality of capture probes that can specifically bind an intrinsic gene expression product. The number of capture probes on the substrate varies with the purpose for which the array is intended. The arrays may be low-density arrays or high-density arrays.

Techniques for the synthesis of these arrays using mechanical synthesis methods are described in, e.g., U.S. Pat. No. 5,384,261, incorporated herein by reference in its entirety for all purposes. The array may be fabricated on a surface of virtually any shape or even a multiplicity of surfaces. Arrays may be probes (e.g., nucleic-acid binding probes) on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. Arrays may be packaged in such a manner as to allow for diagnostics or other manipulation on the device. See, for example, U.S. Pat. Nos. 5,856,174 and 5,922,591, each of which is herein incorporated by reference.

In another embodiment, the kit comprises a set of oligonucleotide primers sufficient for the detection and/or quantitation of each of the 3, 9, 16, or 20 genes listed in Tables 1-4. The oligonucleotide primers may be provided in a lyophilized or reconstituted form, or may be provided as a set of nucleotide sequences. In one embodiment, the primers are provided in a microplate format, where each primer set occupies a well (or multiple wells, as in the case of replicates) in the microplate. The microplate may further comprise primers sufficient for the detection of one or more housekeeping genes as discussed infra. The kit may further comprise reagents and instructions sufficient for the amplification of expression products from the 3, 9, 16, or 20 genes listed in Tables 1-4.

In order to facilitate ready access, e.g., for comparison, review, recovery, and/or modification, the gene expressions are typically recorded in a database. Most typically, the database is a relational database accessible by a computational device, although other formats, e.g., manually accessible indexed files of expression profiles as photographs, analogue or digital imaging readouts, spreadsheets, etc. can be used. Regardless of whether the expression patterns initially recorded are analog or digital in nature, the expression patterns, expression profiles (collective expression patterns), and molecular signatures (correlated expression patterns) are stored digitally and accessed via a database. Typically, the database is compiled and maintained at a central facility, with access being available locally and/or remotely.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMS, DVDs, ROM, RAM, and other memory and computer storage devices. The computer program that may be used to configure the computer to carry out the steps of the methods and/or record the results may also be provided over an electronic network, for example, over the internet, an intranet, or other network.

The present disclosure provides a method for treating a breast cancer in a subject in need thereof, the method comprising the steps of: (a) predicting a risk of breast cancer recurrence in the subject; or (b) stratifying the subject into a low or high risk group of breast cancer recurrence; and (c) administering a treatment to the subject, wherein the treatment is based on (a) or (b). In some embodiments, predicting a risk of breast cancer recurrence in the subject can comprise methods described herein. In some embodiments, stratifying the subject into a low or high risk group of breast cancer recurrence can comprise the methods described herein. In some embodiments, the breast cancer is ER+/HER2− breast cancer. In some embodiments, the treatment is a breast cancer treatment.

The present invention further comprises providing a subject in need a breast cancer treatment. The breast cancer treatment may include one or more anti-cancer or chemotherapeutic agents. Classes of anti-cancer or chemotherapeutic agents can include anthracycline agents, alkylating agents, nucleoside analogs, platinum agents, vinca agents, anti-estrogen drugs, aromatase inhibitors, ovarian suppression agents, endocrine/hormonal agents, bisphophonate therapy agents and targeted biological therapy agents (e.g., antibodies). Specific anti-cancer or chemotherapeutic agents include cyclophosphamide, fluorouracil (or 5-fluorouracil or 5-FU), methotrexate, thiotepa, carboplatin, cisplatin, gemcitabine, anthracycline, taxanes, paclitaxel, protein-bound paclitaxel, doxorubicin, docetaxel, vinorelbine, tamoxifen, raloxifene, toremifene, fulvestrant, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof.

The treatment may include radiation therapy. Preferably, the treatment that includes radiation also includes cyclophosphamide, fluorouracil (or 5-fluorouracil or 5-FU), methotrexate, or combinations thereof. One such combination is CMF which includes cyclophosphamide, methotrexate, and fluorouracil; another such combination is AC which includes doxorubicin and cyclophosphamide.

The treatment may include a surgical intervention.

A "more aggressive" cancer treatment can refer to a specific cancer treatment regimen. A "more aggressive" cancer treatment may comprise a higher dose of an anti-cancer or chemotherapeutic agent. A "more aggressive" cancer treatment may comprise more frequent dosing of an anti-cancer or chemotherapeutic agent. A "more aggressive" cancer treatment may comprise a more potent anti-cancer or chemotherapeutic agent. A "more aggressive" cancer treatment may comprise a plurality of anti-cancer or chemotherapeutic agents. A "more aggressive" cancer treatment may combine a plurality of treatment modalities, e.g., anti-cancer or chemotherapeutic agents along with surgical intervention, anti-cancer or chemotherapeutic agents along with radiation, radiation along with surgical intervention, and anti-cancer or chemotherapeutic agents, surgical intervention, and radiation. Any of the above-mentioned "more aggressive" cancer treatment may be combined with any other above-mentioned "more aggressive" cancer treatments or with other cancer treatments known in the art. A "more aggressive" cancer treatment may comprise administering to the subject adjuvant chemotherapy.

Example 1—the Methods of the Present Disclosure Outperform Existing Prognostic Algorithms The following is an example that describes the development of the SPARE methods of the present disclosure and that demonstrates these methods outperform existing prognostic algorithms in the prediction of distant recurrence of breast cancer.

The SPARE methods of the present disclosure that integrates gene expression data with tumor size and nodal status to derive risk scores for recurrence were developed using a data from ER+/HER2− breast cancer patients (n=1,827) that included a 15-year complete follow-up from the European Institute of Oncology in Milan. The clinico-pathological characteristics and demographics of the patients are shown in Table 5. One third of the patients were randomly assigned to a training set and two-thirds to a validation set. The association between sets (training or validation) and the demographic, clinical, and pathological variables was evaluated using the chi-square test. The number (N) of patients and percentage (%) in each group are indicated in Table 5.

TABLE 5

| Characteristic | All Patients (N = 1827) | Training Set (N = 609) | Validation Set (N = 1218) | p value |
|---|---|---|---|---|
| Age at surgery | | | | 0.51 |
| <50 | 670 (36.7) | 217 (35.6) | 453 (37.2) | |
| ≥50 | 1157 (63.3) | 392 (64.4) | 765 (62.8) | |
| Histology | | | | 0.91 |
| Ductal | 1407 (77.0) | 470 (77.2) | 937 (76.9) | |
| Other subtypes | 420 (23.0) | 139 (22.8) | 281 (23.1) | |
| pT | | | | 0.33 |
| pT1a/b | 266 (14.6) | 97 (15.9) | 169 (13.9) | |
| pT1c | 989 (54.1) | 312 (51.2) | 677 (55.6) | |
| pT2 | 517 (28.3) | 182 (29.9) | 335 (27.5) | |
| pT3/pT4 | 55 (3.0) | 18 (3.0) | 37 (3.0) | |
| pN | | | | 0.82 |
| pN0 | 910 (49.8) | 303 (49.8) | 607 (49.8) | |
| pN1 | 573 (31.4) | 185 (30.4) | 388 (31.9) | |
| pN2/pN3 | 293 (16.0) | 102 (16.7) | 191 (15.7) | |
| pNx | 51 (2.8) | 19 (3.1) | 32 (2.6) | |
| Grade | | | | 0.57 |
| 1 | 418 (22.9) | 140 (23.0) | 278 (22.8) | |
| 2 | 910 (49.8) | 291 (47.8) | 619 (50.8) | |
| 3 | 453 (24.8) | 161 (26.4) | 292 (24.0) | |
| n/a | 46 (2.5) | 17 (2.8) | 29 (2.4) | |
| Lymphovascular invasion | | | | 0.88 |
| Absent | 1276 (69.8) | 424 (69.6) | 852 (70.0) | |
| Present | 551 (30.2) | 185 (30.4) | 366 (30.0) | |
| Ki-67 | | | | 0.72 |
| <14% | 627 (34.3) | 213 (35.0) | 414 (34.0) | |
| ≥14% | 1199 (65.6) | 396 (65.0) | 803 (65.9) | |
| n/a | 1 (0.1) | 0 (0.0) | 1 (0.1) | |
| Surgery | | | | 0.29 |
| Quadrantectomy | 1524 (83.4) | 500 (82.1) | 1024 (84.1) | |
| Mastectomy | 303 (16.6) | 109 (17.9) | 194 (15.9) | |
| Hormone therapy | | | | 0.41 |
| No | 136 (7.4) | 41 (6.7) | 95 (7.8) | |
| Yes | 1691 (92.6) | 568 (93.3) | 1123 (92.2) | |
| Adjuvant chemotherapy | | | | 0.37 |
| No | 867 (47.5) | 298 (48.9) | 569 (46.7) | |
| Yes | 960 (52.5) | 311 (51.1) | 960 (53.3) | |
| Adjuvant radiotherapy | | | | 0.27 |
| No | 314 (17.2) | 113 (36.0) | 201 (64.0) | |
| Yes | 1513 (82.8) | 496 (32.8) | 1017 (67.2) | |

The SPARE methods of the present disclosure were generated by determining a continuous function in the training set with the use of a Cox Hazards regression model in which patients' follow-up was censored after 15 years. FIG. 1 shows the predicted risk of distant recurrence as a continuous function of the SPARE recurrence score, with 95% confidence intervals. The dashed curves and shaded areas in FIG. 1 indicate the 95 percent confidence interval. The cut-off values for the determination of the low risk and high risk groups corresponds respectively to the values of the recurrence score for which the 95% upper bound and 95% lower bound cross the horizontal 10% risk line. The rug plot on the top of the x axis shows the recurrence score for individual patients in the training set.

Figure 2:
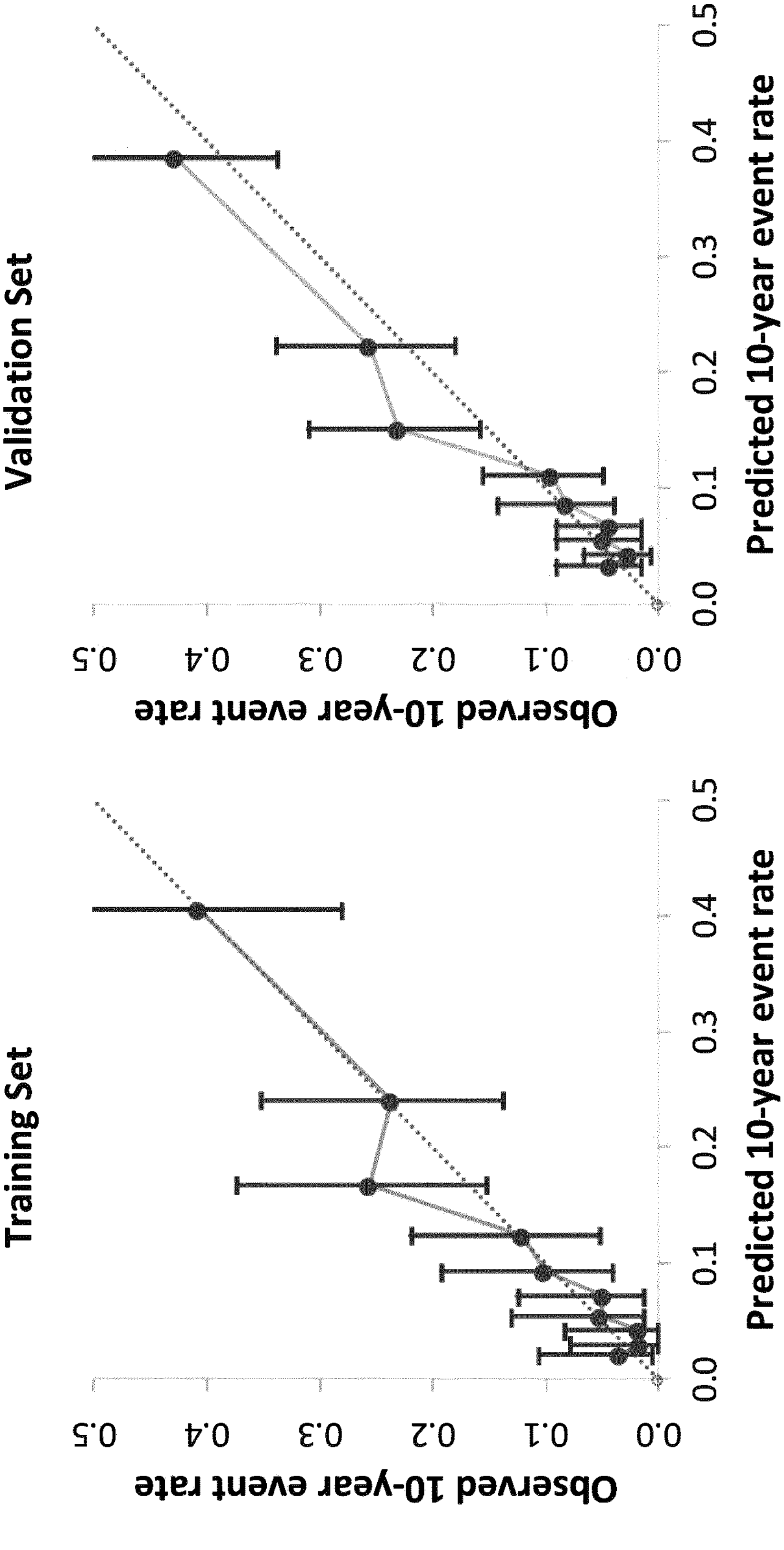
FIG. 2 is a series of graphs showing the results of the calibration prediction plot analysis of observed versus predicted 10-year distant metastasis rate according to the SPARE methods of the present disclosure in both the training and validation datasets.

To measure how much the prognostic estimation of the SPARE model matches the real outcome probability, a calibration plot analysis was performed comparing observed versus predicted 10-year distant metastasis rate according to the SPARE methods of the present disclosure in both the training and validation datasets. As shown in FIG. 2, the SPARE method reliably predicts recurrence over the span of 10 years.

The performance of the SPARE methods of the present disclosure for predicting distant recurrence in the training and validation sets, as well as in groups treated with adjuvant chemotherapy or not treated with adjuvant chemotherapy, are summarized in Table 6. The results in Table 6 indicate that the SPARE methods of the present disclosure can accurately predict distant recurrence of breast cancer at 10 years.

TABLE 6

| Class of Risk | No. of Patients (%) | Rate of distant recurrence at 10 years (95% CI) | Hazards Ratio (95% CI) | Distant recurrences at 10 years Observed | Predicted |
|---|---|---|---|---|---|
| Training Set | 609 | | | | |
| Low risk | 275 (45.2) | 2.6 (1.3-5.3) | 1.00 | 7 | 11.5 |
| Intermediate risk | 122 (20.0) | 8.4 (4.3-14.2) | 3.11 (1.31-7.36) | 10 | 12.0 |
| High risk | 212 (34.8) | 28.7 (22.7-35.0) | 11.3 (5.65-22.5) | 59 | 55.0 |

TABLE 6-continued

| Class of Risk | No. of Patients (%) | Rate of distant recurrence at 10 years (95% CI) | Hazards Ratio (95% CI) | Distant recurrences at 10 years Observed | Predicted |
|---|---|---|---|---|---|
| Validation Set | 1218 | | | | |
| Low risk | 579 (47.5) | 3.2 (2.0-4.9) | 1.00 | 18 | 25.5 |
| Intermediate risk | 260 (21.4) | 8.3 (5.2-12.2) | 2.29 (1.30-4.05) | 20 | 25.1 |
| High risk | 379 (31.1) | 29.6 (25.0-34.4) | 8.57 (5.52-13.3) | 109 | 99.3 |
| No adjuvant chemotherapy | 960 | | | | |
| Low risk | 605 (69.8) | 2.7 (1.6-4.3) | 1.00 | 16 | 23.7 |
| Intermediate risk | 145 (16.7) | 8.7 (4.7-14.1) | 2.73 (1.37-5.46) | 12 | 14.0 |
| High risk | 117 (13.5) | 24.7 (17.1-32.9) | 8.26 (4.72-14.4) | 28 | 26.0 |
| Adjuvant chemotherapy | 867 | | | | |
| Low risk | 249 (25.9) | 3.7 (1.8-6.4) | 1.00 | 9 | 13.3 |
| Intermediate risk | 237 (24.7) | 8.1 (5.0-12.1) | 2.05 (1.02-4.13) | 18 | 23.1 |
| High risk | 474 (49.4) | 30.4 (26.3-34.7) | 7.89 (4.39-14.2) | 140 | 128.4 |

The Clinical Treatment Score (CTS) is a prognostic algorithm based on clinicopathological variables that is widely used by clinicians to predict late distant metastasis for women with ER+breast cancer. CTS is regarded by those of CTS integrates information on nodal status, grade, proliferation status, HER2 status, tumor size, age, and endocrine treatment with tamoxifen or anastrozole. It was developed in the TransATAC cohort to allow head-to-head comparison of genomic predictors with clinico-pathological parameters (see Cuzick J, et al., Prognostic value of a combined estrogen receptor, progesterone receptor, Ki-67, and human epidermal growth factor receptor-2 immunohistochemical score and comparison with the Genomic Health recurrence score in early breast cancer. J Clin Oncol. 2011; 29 (32): 4273-4278).

The performance of the SPARE methods of the present disclosure were compared to the performance of CTS. A summary of the comparison is shown in Table 7

TABLE 7

| | # of Patients | No of DRs | SPARE alone LRA$\chi$2 | SPARE alone P | CTS alone LRA$\chi$2 | CTS alone P | SPARE + CTS vs CTS LRA$\chi$2 | SPARE + CTS vs CTS P | CTS + SPARE vs SPARE LRA$\chi$2 | CTS + SPARE vs SPARE P |
|---|---|---|---|---|---|---|---|---|---|---|
| All patients | 1827 | 248 | 218.40 | <0.0001 | 173.83 | <0.0001 | 46.17 | <0.0001 | 1.60 | 0.21 |
| Data set | | | | | | | | | | |
| Training set | 609 | 87 | 76.77 | <0.0001 | 55.75 | <0.0001 | 21.05 | <0.0001 | 0.02 | 0.88 |
| Validation set | 1218 | 161 | 141.17 | <0.0001 | 118.08 | <0.0001 | 25.24 | <0.0001 | 2.15 | 0.14 |
| Chemotherapy | | | | | | | | | | |
| No | 867 | 63 | 55.63 | <0.0001 | 48.88 | <0.0001 | 9.48 | 0.002 | 2.73 | 0.10 |
| Yes | 960 | 185 | 106.77 | <0.0001 | 74.30 | <0.0001 | 32.65 | <0.0001 | 0.18 | 0.67 |
| pN | | | | | | | | | | |
| pN0/pNx | 961 | 63 | 47.58 | <0.0001 | 27.53 | <0.0001 | 21.30 | <0.0001 | 1.25 | 0.26 |
| pN1 | 573 | 84 | 30.56 | <0.0001 | 15.08 | 0.0001 | 15.53 | <0.0001 | 0.05 | 0.82 |
| pN2/pN3 | 293 | 101 | 16.22 | <0.0001 | 10.06 | 0.002 | 7.11 | 0.008 | 0.95 | 0.33 |

The LRAx2 values in Table 7 (for instance SPARE=218.4 vs. CTS=173.83 in all patients) are to an absolute quantitative measure of the prognostic power of both methods. Therefore, the LRAx2 values associated to SPARE or CTS are compared in univariate analysis one against the other. Thus, as shown in Table 7, the SPARE methods of the present disclosure have superior prognostic power compared to CTS (218.4 vs 173.83, all patients). Moreover, if the information derived from the CTS algorithm is added to the information derived from the SPARE methods, there is no increase in statistically significant information (LRA$\chi$2=1.60, which is below the significant LRAx2 cut-off of 3.84). Conversely, if the information from the SPARE methods are added to the information from the CTS algorithm, there is a significant gain of information (46.17), indicating that SPARE adds prognostic information to CTS. Taken together, these results indicate that the SPARE methods of the present disclosure outperform CTS and provide the most prognostic information for distant recurrence of breast cancer.

Figure 3:
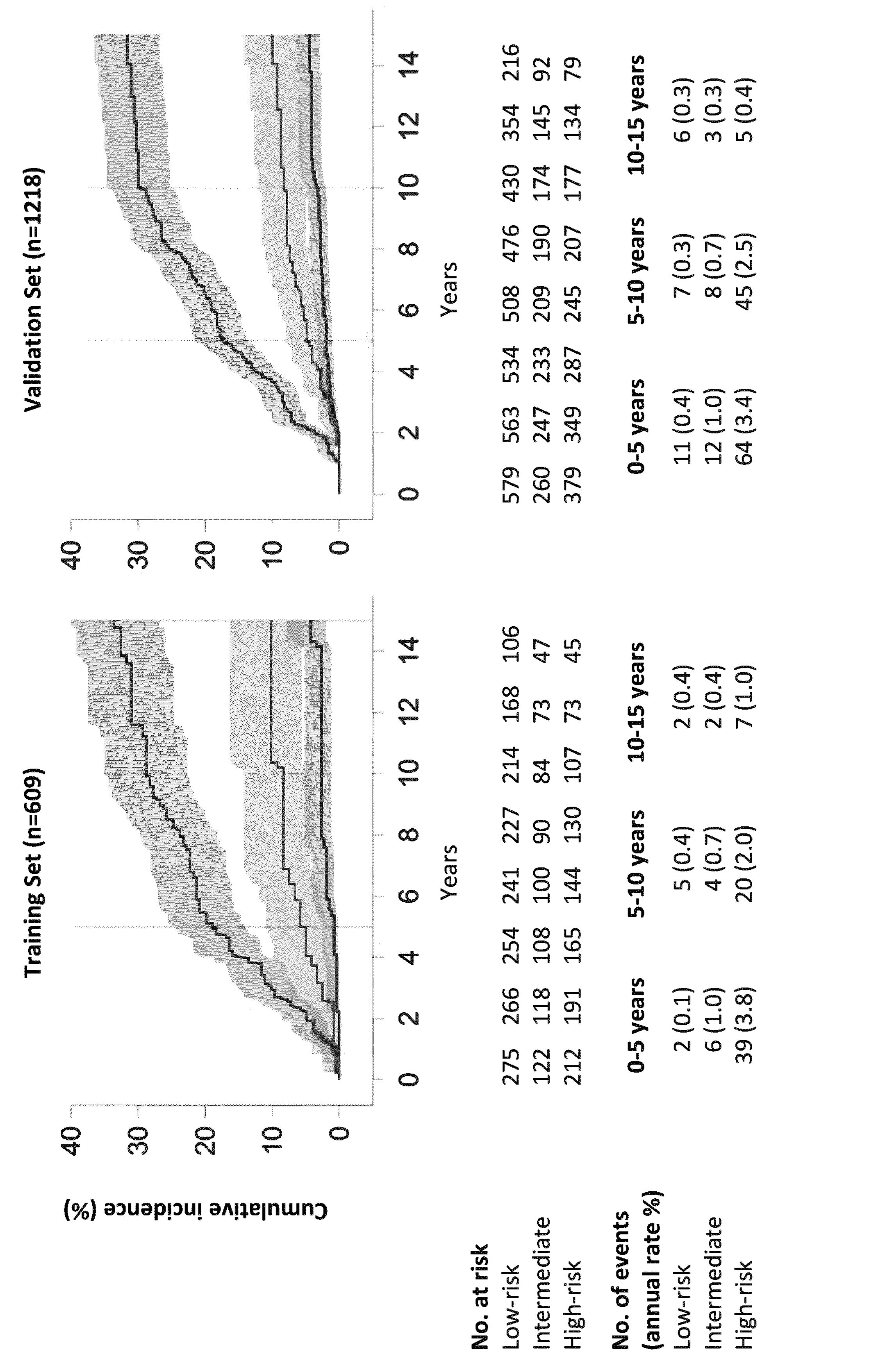
FIG. 3 is a series of graphs showing the cumulative incidence of distant recurrences according to the SPARE methods of the present disclosure in both the training and validation datasets.

FIG. 3. shows the cumulative incidence of distant metastasis over a 10-year period in the training and validation sets according to the SPARE methods of the present disclosure.

Figure 4:
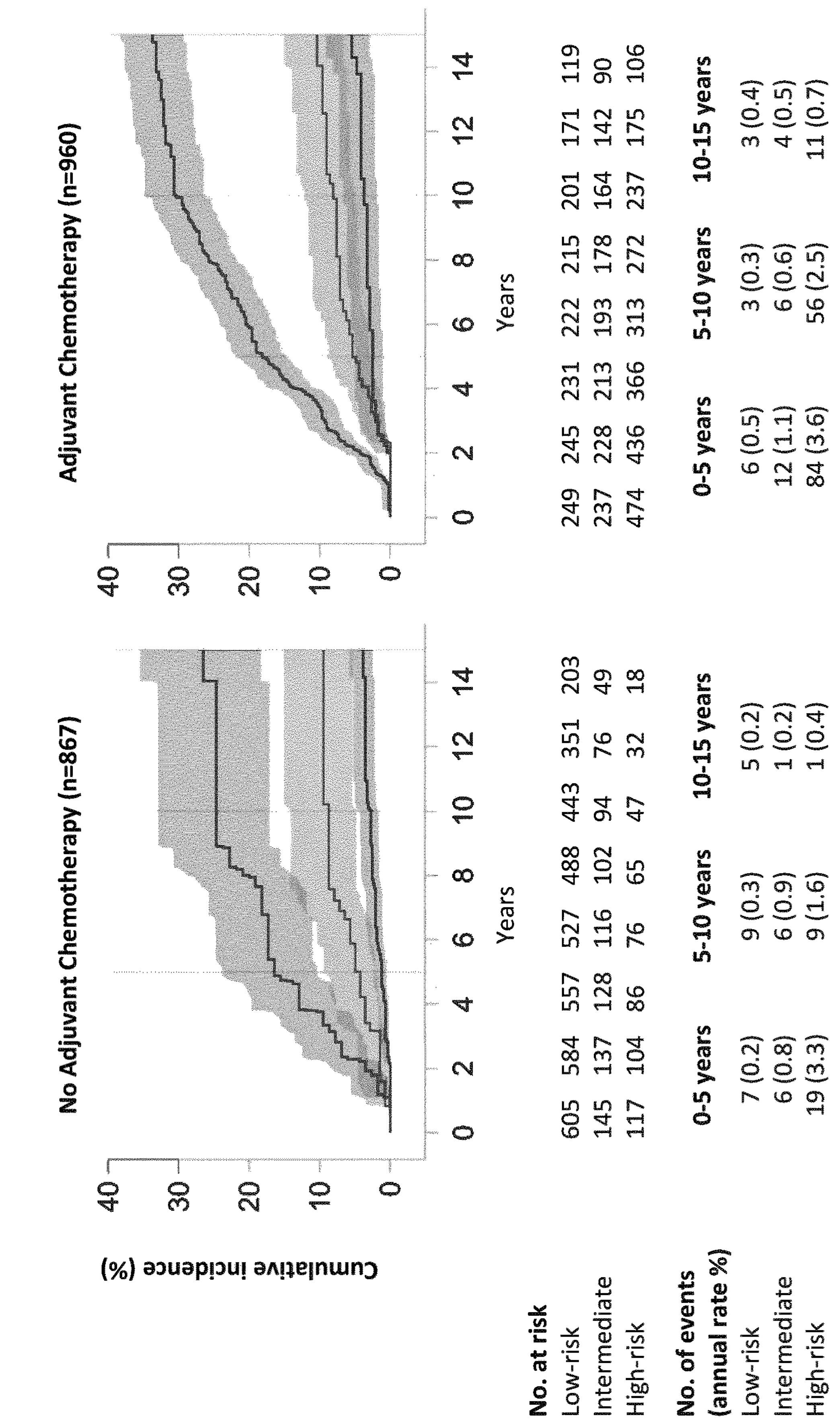
FIG. 4 is a series of graphs showing the cumulative incidence of distant recurrences according to SPARE methods of the present disclosure and the use of chemotherapy in the combined dataset.

The SPARE methods of the present disclosure were also used to analyze patients in the dataset stratified according to treatments. The treatments were decided per the physician's choice based on the estimation of the intrinsic risk of the patients according to standard clinical guidelines (i.e. standard clinicopathological parameters). The results of this analysis are shown in FIG. 4. As shown in the left panel of FIG. 4, in patients that did not receive adjuvant chemotherapy because their physicians deemed them to be low risk based on their clinicopathological characteristics, the SPARE methods of the present disclosure correctly identifies not only patients who did not need adjuvant chemotherapy, but also identifies patients with a high likelihood of recurrence who might have benefited from more aggressive treatments.

Figure 5:
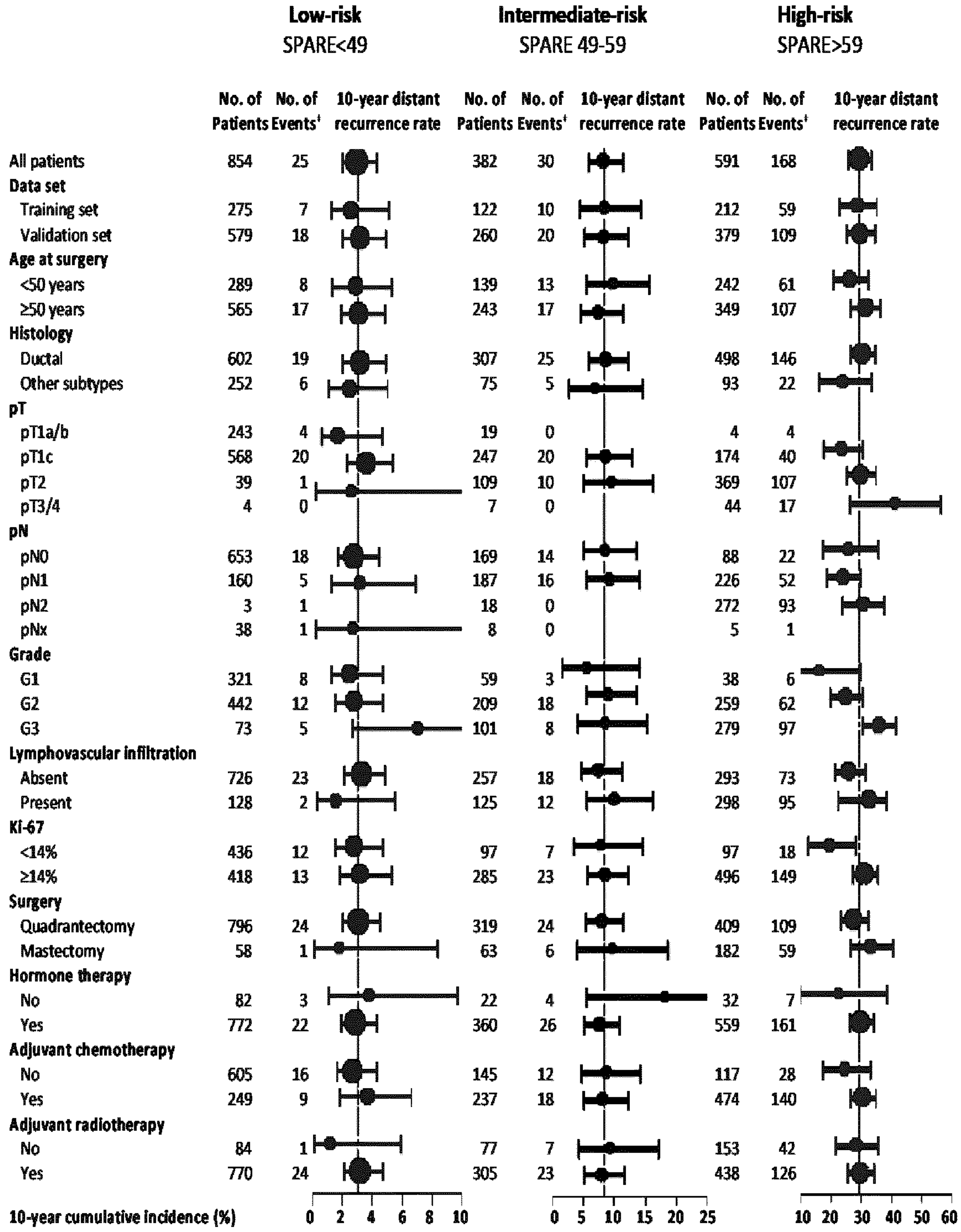
FIG. 5 is forest plot analysis showing 10-year distant recurrence rates according to the SPARE methods of the present disclosure in the different risk groups and stratified according to clinicopathological characteristics.

FIG. 5 shows the results of a forest plot analysis showing 10-year distant recurrence rates, according to the SPARE methods of the present disclosure, in the different risk groups in the entire population and stratified according to clinicopathological characteristics.

The prognostic information provided by the SPARE methods of the present disclosure was also compared with the prognostic information provided by the StemPrintER risk score described in US Patent Application Publication No. 2019-0161809 and International Patent Application Publication No. WO2017/220492. The results of this comparison are summarized in Table 8.

TABLE 8

| | No of | No of | StemPrintER alone | | SPARE alone | | SPARE + StemPrintER vs StemPrintER | | StemPrintER + SPARE vs SPARE | |
|---|---|---|---|---|---|---|---|---|---|---|
| | Patients | DRs | LRΔχ2 | P | LRΔχ2 | P | LRΔχ2 | P | LRΔχ2 | P |
| All patients | 1827 | 248 | 106.58 | <0.0001 | 218.40 | <0.0001 | 113.46 | <0.0001 | 1.63 | 0.20 |
| Data set | | | | | | | | | | |
| Training set | 609 | 87 | 40.22 | <0.0001 | 76.77 | <0.0001 | 36.56 | <0.0001 | 0.00 | 1.00 |
| Validation set | 1218 | 161 | 66.20 | <0.0001 | 141.17 | <0.0001 | 77.23 | <0.0001 | 2.25 | 0.13 |
| Chemotherapy | | | | | | | | | | |
| No | 867 | 63 | 21.00 | <0.0001 | 55.63 | <0.0001 | 37.48 | <0.0001 | 2.84 | 0.091 |
| Yes | 960 | 185 | 56.51 | <0.0001 | 106.77 | <0.0001 | 50.32 | <0.0001 | 0.05 | 0.82 |
| pN | | | | | | | | | | |
| pN0/pNx | 961 | 63 | 37.38 | <0.0001 | 47.58 | <0.0001 | 10.32 | 0.001 | 0.12 | 0.73 |
| pN1 | 573 | 84 | 23.01 | <0.0001 | 30.56 | <0.0001 | 7.73 | 0.005 | 0.18 | 0.67 |
| pN2/pN3 | 293 | 101 | 11.90 | 0.0006 | 16.22 | <0.0001 | 4.71 | 0.030 | 0.39 | 0.53 |

The results in Table 8 show that the SPARE methods of the present disclosure provide more prognostic information than the StemPrintER risk score on its own.

What is claimed is:

1. A method comprising:

(a) determining, in a sample from a subject having at least one ER+/HER2− breast cancer tumor, mRNA expression levels of the following genes: H2AFZ, CDK1, EXOSC4, PHLDA2, APOBEC3B, EIF4EBP1, SFN, PHB, EPB41L5, RACGAP1, MRPS23, TOP2A, H2AFJ, NOL3, MIEN1, CENPW, LY6E, ALYREF, MMP1, and NDUFB10;

(b) determining the tumor size (pT) of the at least one ER+/HER2− breast cancer tumor;

(c) determining the nodal status (pN) of the at least one ER+/HER2− breast cancer tumor; and (d) calculating a risk score for ER+/HER2− breast cancer recurrence based upon the mRNA expression levels of H2AFZ, CDK1, EXOSC4, PHLDA2, APOBEC3B, EIF4EBP1, SFN, PHB, EPB41L5, RACGAP1, MRPS23, TOP2A, H2AFJ, NOL3, MIEN1, CENPW, LY6E, ALYREF, MMP1, and NDUFB10, the pT and the pN; and (e) administering at least one treatment to the subject based on the risk score, wherein the treatment comprises surgery, radiation, anthracycline agents, alkylating agents, nucleoside analogs, platinum agents, vinca agents, anti-estrogen drugs, aromatase inhibitors, ovarian suppression agents, endocrine/hormonal agents, bisphophonate therapy agents, cyclophosphamide, fluorouracil (or 5-fluorouracil or 5-FU), methotrexate, thiotepa, carboplatin, cisplatin, gemcitabine, anthracycline, taxanes, paclitaxel, protein-bound paclitaxel, doxorubicin, docetaxel, vinorelbine, tamoxifen, raloxifene, toremifene, fulvestrant, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof, wherein the risk score is calculated according to the following formula:

$$\text{Risk Score} = \frac{(0.03604) \times \left(\sum_i \beta_i \times Cq_{normalized}\right) + pT + pN}{5.64032}$$

wherein i is the summation index for the genes for which the mRNA expression level was measured;

β is the ridge penalized Cox model coefficient for each gene as set forth below:

H2AFZ-0.03833591325196550, CDK1-0.06132455806571770, EXOSC4-0.02105976326055420, PHLDA2-0.06295739658169650, APOBEC3B 0.02341881674020150, EIF4EBP1-0.13911217901125500, SFN 0.05788269046891110, PHB-0.03538557745953510, EPB41L5-0.04675539403890050, RACGAP1-0.05097505893853430, MRPS23-0.14201022110072700, TOP2A-0.11290078348786600, H2AFJ-0.04975471358452700, NOL3-0.04193802459521500, MIEN1 0.01133668644106850, CENPW-0.03717918353187610, LY6E-0.02829256296234230, ALYREF-0.09541915699494330, MMP1-0.00911370427072023, NDUFB10 0.00626166874136819;

and $Cq_{normalized}$ is the normalized average quantification cycle (Cq) for each of the genes for which the mRNA expression level was measured;

wherein pT is 0.45542 when the tumor size of the at least one ER+/HER2− breast cancer tumor is determined to be pT1c; or pT is 0.96572 when the tumor size of the ER+/HER2− breast cancer tumor is determined to be any of pT2, pT3 and pT4; and wherein pN is 0.46293 when the nodal status of the at least one ER+/HER2− breast cancer tumor is determined to be pN1 or pN is 1.24922 when the nodal status of the at least one ER+/HER2− breast cancer tumor is determined to be pN2.

2. The method of claim 1, wherein $Cq_{normalized}$ is normalized to the expression of at least two reference genes.

3. The method of claim 2, wherein the at least two reference genes are each (a) housekeeping genes; or (b) selected from the group consisting of GAPDH, GUSB, HPRTI, and TBP.

4. The method of claim 1, wherein $Cq_{normalized}$ is calculated according to the following formula:

$$Cq_{normalized} = AVG\ Cq - SF$$

wherein SF is the difference between the AVG Cq value of the at least two reference genes for each subject and a constant reference value K.

5. The method of claim 4, wherein (a) K is the mean of the AVG Cq of the at least two reference genes calculated across a plurality of training samples or (b) wherein K=25.012586069.

6. The method of claim 1, wherein the mRNA expression levels are determined using one or more techniques selected from the group consisting of analysis of single strand conformation polymorphism, capillary electrophoresis, denaturing high performance liquid chromatography, digital molecular barcoding technology, direct sequencing, DNA mismatch-binding protein assays, dynamic allele-specific hybridization, Fluorescent in situ hybridization (FISH), high-density oligonucleotide SNP arrays, high-resolution melting analysis, microarray, next generation sequencing (NGS), Northern blot analysis, nuclease protection analysis, oligonucleotide ligase assays, polymerase chain reaction (PCR), primer extension assays, Quantigene analysis, quantitative nuclease-protection assay (qNPA), reporter gene detection, restriction fragment length polymorphism (RFLP) assays, reverse transcription and real-time quantitative polymerase chain reaction (RT-qPCR), reverse transcription-polymerase chain reaction (RT-PCR), RNA sequencing (RNA-seq), Serial analysis of gene expression (SAGE), Single Molecule Real Time (SMRT) DNA sequencing technology, SNPLex, Southern blot analysis, Sybr Green chemistry, TaqMan-based assays, temperature gradient gel electrophoresis (TGGE), and Tiling array.

7. A method for stratifying a subject having at least one ER+/HER2− breast cancer tumor into a low or high risk group of ER+/HER2− breast cancer recurrence, the method comprising:

(a) determining, in a sample from the subject, mRNA expression levels of the following genes: H2AFZ, CDK1, EXOSC4, PHLDA2, APOBEC3B, EIF4EBP1, SFN, PHB, EPB41L5, RACGAP1, MRPS23, TOP2A, H2AFJ, NOL3, MIEN1, CENPW, LY6E, ALYREF, MMP1, and NDUFB10;

(b) determining the tumor size (pT) of the at least one ER+/HER2− breast cancer tumor;

(c) determining the nodal status (pN) of the at least one ER+/HER2− breast cancer tumor;

(d) calculating a risk score based upon the mRNA expression levels of H2AFZ, CDK1, EXOSC4, PHLDA2, APOBEC3B, EIF4EBP1, SFN, PHB, EPB41L5, RACGAP1, MRPS23, TOP2A, H2AFJ, NOL3, MIEN1, CENPW, LY6E, ALYREF, MMP1, and NDUFB10, the pT and the pN;

(e) stratifying the subject based upon the calculated risk score; and (f) administering at least one treatment to the subject based on the risk score, wherein the treatment comprises surgery, radiation, anthracycline agents, alkylating agents, nucleoside analogs, platinum agents, vinca agents, anti-estrogen drugs, aromatase inhibitors, ovarian suppression agents, endocrine/hormonal agents, bisphophonate therapy agents, cyclophosphamide, fluorouracil (or 5-fluorouracil or 5-FU), methotrexate, thiotepa, carboplatin, cisplatin, gemcitabine, anthracycline, taxanes, paclitaxel, protein-bound paclitaxel, doxorubicin, docetaxel, vinorelbine, tamoxifen, raloxifene, toremifene, fulvestrant, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof, wherein the risk score is calculated according to the following formula:

$$\text{Risk Score} = \frac{(0.03604) \times \left(\sum_i \beta_i \times Cq_{normalized}\right) + pT + pN}{5.64032}$$

wherein i is the summation index for the genes for which the mRNA expression level was measured;

β is the ridge penalized Cox model coefficient for each gene as set forth below:

H2AFZ-0.03833591325196550, CDK1-0.06132455806571770, EXOSC4-0.02105976326055420, PHLDA2-0.06295739658169650, APOBEC3B 0.02341881674020150, EIF4EBP1-0.13911217901125500, SEN 0.05788269046891110, PHB-0.03538557745953510, EPB41L5-0.04675539403890050, RACGAP1-0.05097505893853430, MRPS23-0.14201022110072700, TOP2A-0.11290078348786600, H2AFJ-0.04975471358452700, NOL3-0.04193802459521500, MIEN1 0.01133668644106850, CENPW-0.03717918353187610, LY6E-0.02829256296234230, ALYREF-0.09541915699494330, MMP1-0.00911370427072023, NDUFB10 0.00626166874136819;

and $Cq_{normalized}$ is the normalized average quantification cycle (Cq) for each of the genes for which the mRNA expression level was measured;

wherein pT is 0.45542 when the tumor size of the at least one ER+/HER2− breast cancer tumor is determined to be pT1c; or pT is 0.96572 when the tumor size of the ER+/HER2− breast cancer tumor is determined to be any of pT2, pT3 and pT4; and wherein pN is 0.46293 when the nodal status of the at least one ER+/HER2− breast cancer tumor is determined to be pN1 or pN is 1.24922 when the nodal status of the at least one ER+/HER2− breast cancer tumor is determined to be pN2.

8. The method of claim 7, wherein stratifying the subject based upon the calculated risk score comprises (a) stratifying the subject as having a low risk for ER+/HER2− breast cancer recurrence when the risk score is less than a predetermined cutoff value and/or (b) stratifying the subject as having a high risk for ER+/HER2− breast cancer recurrence when the risk score is greater than a predetermined cutoff value.

9. The method of claim 7, wherein $Cq_{normalized}$ is normalized to the expression of at least two reference genes.

10. The method of claim 9, wherein the at least two reference genes are (a) housekeeping genes or (b) selected from the group consisting of GAPDH, GUSB, HPRT1, and TBP.

11. The method of claim 7, wherein $Cq_{normalized}$ is calculated according to the following formula:

$$Cq_{normalized} = AVG\ Cq - SF$$

wherein SF is the difference between the AVG Cq value of the at least two reference genes for each subject and a constant reference value K.

12. The method of claim 11, wherein (a) K is the mean of the AVG Cq of the at least two reference genes calculated across a plurality of training samples or (b) wherein K=25.012586069.

13. The method of claim 7, wherein the mRNA expression levels are determined using one or more techniques selected from the group consisting of analysis of single strand conformation polymorphism, capillary electrophoresis, denaturing high performance liquid chromatography, digital molecular barcoding technology, direct sequencing, DNA mismatch-binding protein assays, dynamic allele-specific hybridization, Fluorescent in situ hybridization (FISH), high-density oligonucleotide SNP arrays, high-resolution melting analysis, microarray, next generation sequencing (NGS), Heliscope instrument, Northern blot analysis, nuclease protection analysis, oligonucleotide ligase assays, polymerase chain reaction (PCR), primer extension assays, Quantigene analysis, quantitative nuclease-protection assay (qNPA), reporter gene detection, restriction fragment length polymorphism (RFLP) assays, reverse transcription and real-time quantitative polymerase chain reaction (RT-qPCR), reverse transcription-polymerase chain reaction (RT-PCR), RNA sequencing (RNA-seq), Serial analysis of gene expression (SAGE), Single Molecule Real Time (SMRT) DNA sequencing technology, SNPLex, Southern blot analysis, Sybr Green chemistry, TaqMan-based assays, temperature gradient gel electrophoresis (TGGE), and Tiling array.

14. A method for stratifying a subject having at least one ER+/HER2− breast cancer tumor into a low, intermediate, or high risk group of ER+/HER2− breast cancer recurrence, the method comprising:

(a) determining, in a sample from the subject, mRNA expression levels of the following genes: H2AFZ, CDK1, EXOSC4, PHLDA2, APOBEC3B, EIF4EBP1, SFN, PHB, EPB41L5, RACGAP1, MRPS23, TOP2A, H2AFJ, NOL3, MIEN1, CENPW, LY6E, ALYREF, MMP1, and NDUFB10;

(b) determining the tumor size (pT) of the at least one ER+/HER2− breast cancer tumor;

(c) determining the nodal status (pN) of the at least one ER+/HER2− breast cancer tumor;

(d) calculating a risk score based upon the mRNA expression levels of H2AFZ, CDK1, EXOSC4, PHLDA2, APOBEC3B, EIF4EBP1, SFN, PHB, EPB41L5, RACGAP1, MRPS23, TOP2A, H2AFJ, NOL3, MIEN1, CENPW, LY6E, ALYREF, MMP1, and NDUFB10, the pT and the pN;

(e) stratifying the subject based upon the calculated risk score; and (f) administering at least one treatment to the subject based on the risk score, wherein the treatment comprises surgery, radiation, anthracycline agents, alkylating agents, nucleoside analogs, platinum agents, vinca agents, anti-estrogen drugs, aromatase inhibitors, ovarian suppression agents, endocrine/hormonal agents, bisphophonate therapy agents, cyclophosphamide, fluorouracil (or 5-fluorouracil or 5-FU), methotrexate, thiotepa, carboplatin, cisplatin, gemcitabine, anthracycline, taxanes, paclitaxel, protein-bound paclitaxel, doxorubicin, docetaxel, vinorelbine, tamoxifen, raloxifene, toremifene, fulvestrant, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof, wherein the risk score is calculated according to the following formula:

$$\text{Risk Score} = \frac{(0.03604)\times\left(\sum_i \beta_i \times Cq_{normalized}\right) + pT + pN}{5.64032}$$

wherein i is the summation index for the genes for which the mRNA expression level was measured;

β is the ridge penalized Cox model coefficient for each gene as set forth below:

H2AFZ-0.03833591325196550, CDK1-0.06132455806571770, EXOSC4-0.02105976326055420, PHLDA2-0.06295739658169650, APOBEC3B 0.02341881674020150, EIF4EBP1-0.13911217901125500, SEN 0.05788269046891110, PHB-0.03538557745953510, EPB41L5-0.04675539403890050, RACGAP1-0.05097505893853430, MRPS23-0.14201022110072700, TOP2A-

0.11290078348786600, H2AFJ-0.04975471358452700, NOL3-0.04193802459521500, MIEN1 0.01133668644106850, CENPW-0.03717918353187610, LY6E-0.02829256296234230, ALYREF-0.09541915699494330, MMP1-0.00911370427072023, NDUFB10 0.00626166874136819;

and $Cq_{normalized}$ is the normalized average quantification cycle (Cq) for each of the genes for which the mRNA expression level was measured;

wherein pT is 0.45542 when the tumor size of the at least one ER+/HER2− breast cancer tumor is determined to be pT1c; or pT is 0.96572 when the tumor size of the ER+/HER2− breast cancer tumor is determined to be any of pT2, pT3 and pT4; and wherein pN is 0.46293 when the nodal status of the at least one ER+/HER2− breast cancer tumor is determined to be pN1 or pN is 1.24922 when the nodal status of the at least one ER+/HER2− breast cancer tumor is determined to be pN2.

15. The method of claim 14, wherein stratifying the subject based upon the calculated risk score comprises (a) stratifying the subject as having a low risk for ER+/HER2− breast cancer recurrence when the risk score is less than a first predetermined cutoff value; (b) stratifying the subject as having a high risk for ER+/HER2− breast cancer recurrence when the risk score is greater than a second predetermined cutoff value and/or (c) stratifying the subject as having an intermediate risk for ER+/HER2− breast cancer recurrence when the risk score is greater than or equal to a first predetermined cutoff value and less than or equal to a second predetermined cutoff value.

16. The method of claim 14, wherein $Cq_{normalized}$ is normalized to the expression of at least two reference genes.

17. The method of claim 16, wherein the at least two reference genes are (a) housekeeping genes or (b) selected from the group consisting of GAPDH, GUSB, HPRTI, and TBP.

18. The method of claim 14, wherein $Cq_{normalized}$ is calculated according to the following formula:

$$Cq_{normalized} = AVG\ Cq - SF$$

wherein SF is the difference between the AVG Cq value of the at least two reference genes for each subject and a constant reference value K.

19. The method of claim 18, wherein (a) K is the mean of the AVG Cq of the at least two reference genes calculated across a plurality of training samples or (b) wherein K=25.012586069.

20. The method of claim 14, wherein the mRNA expression levels are determined using one or more techniques selected from the group consisting of analysis of single strand conformation polymorphism, capillary electrophoresis, denaturing high performance liquid chromatography, digital molecular barcoding technology, direct sequencing, DNA mismatch-binding protein assays, dynamic allele-specific hybridization, Fluorescent in situ hybridization (FISH), high-density oligonucleotide SNP arrays, high-resolution melting analysis, microarray, next generation sequencing (NGS), Northern blot analysis, nuclease protection analysis, oligonucleotide ligase assays, polymerase chain reaction (PCR), primer extension assays, Quantigene analysis, quantitative nuclease-protection assay (qNPA), reporter gene detection, restriction fragment length polymorphism (RFLP) assays, reverse transcription and real-time quantitative polymerase chain reaction (RT-qPCR), reverse transcription-polymerase chain reaction (RT-PCR), RNA sequencing (RNA-seq), Serial analysis of gene expression (SAGE), Single Molecule Real Time (SMRT) DNA sequencing technology, SNPLex, Southern blot analysis, Sybr Green chemistry, TaqMan-based assays, temperature gradient gel electrophoresis (TGGE), and Tiling array.

* * * * *